US008841123B2

(12) United States Patent
Stern et al.

(10) Patent No.: US 8,841,123 B2
(45) Date of Patent: *Sep. 23, 2014

(54) METHODS FOR CULTURING UNDIFFERENTIATED CELLS USING SUSTAINED RELEASE COMPOSITIONS

(71) Applicant: Regenerative Research Foundation, Rensselaer, NY (US)

(72) Inventors: Jeffrey Stern, Slingerlands, NY (US); Sally Temple Stern, Slingerlands, NY (US)

(73) Assignee: Regenerative Research Foundation, Rensselaer, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/915,826

(22) Filed: Jun. 12, 2013

(65) Prior Publication Data
US 2013/0337562 A1    Dec. 19, 2013

Related U.S. Application Data

(63) Continuation of application No. 13/175,667, filed on Jul. 1, 2011, now Pat. No. 8,481,308.

(60) Provisional application No. 61/360,741, filed on Jul. 1, 2010.

(51) Int. Cl.
*C12N 5/00* (2006.01)
*C12N 5/074* (2010.01)
*C12N 5/0735* (2010.01)
*C12N 5/079* (2010.01)
*C12N 5/0797* (2010.01)

(52) U.S. Cl.
CPC .......... *C12N 5/0623* (2013.01); *C12N 2531/00* (2013.01); *C12N 2501/606* (2013.01); *C12N 2501/604* (2013.01); *C12N 2501/603* (2013.01); *C12N 5/0696* (2013.01); *C12N 5/0606* (2013.01); *C12N 2533/40* (2013.01); *C12N 5/0621* (2013.01); *C12N 2501/115* (2013.01); *C12N 2506/1307* (2013.01); *C12N 2501/602* (2013.01)
USPC .......................................... 435/325; 435/384

(58) Field of Classification Search
USPC ................................................ 435/325, 384
See application file for complete search history.

(56) References Cited

U.S. PATENT DOCUMENTS

| 4,298,822 | A | 11/1981 | Fukuda |
| 5,071,743 | A | 12/1991 | Slilaty et al. |
| 5,356,635 | A | 10/1994 | Raman et al. |
| 5,702,931 | A | 12/1997 | Andrews et al. |
| 5,780,270 | A | 7/1998 | Lesley |
| 5,789,166 | A | 8/1998 | Bauer et al. |
| 5,843,780 | A | 12/1998 | Thomson |
| 5,932,419 | A | 8/1999 | Bauer et al. |
| 6,165,747 | A | 12/2000 | Ingham et al. |
| 6,200,806 | B1 | 3/2001 | Thomson |
| 6,242,222 | B1 | 6/2001 | Gifford |
| 6,271,363 | B1 | 8/2001 | Ingham et al. |
| 6,337,539 | B1 | 1/2002 | Yorifuji et al. |
| 6,664,075 | B2 | 12/2003 | Ingham et al. |
| 7,029,913 | B2 | 4/2006 | Thomson |
| 7,226,617 | B2 | 6/2007 | Ding et al. |
| 8,481,308 | B2 * | 7/2013 | Stern et al. .................... 435/325 |
| 2002/0057059 | A1 | 5/2002 | Ogishi et al. |
| 2003/0134414 | A1 | 7/2003 | Ferguson |
| 2003/0220280 | A1 | 11/2003 | Bunge et al. |
| 2005/0095706 | A1 | 5/2005 | Zhang et al. |
| 2005/0208545 | A1 | 9/2005 | Beachy |
| 2005/0277189 | A1 | 12/2005 | Temple et al. |
| 2006/0069009 | A1 | 3/2006 | Messina et al. |
| 2006/0182724 | A1 | 8/2006 | Riordan |
| 2007/0254842 | A1 | 11/2007 | Bankiewicz |
| 2008/0293624 | A1 | 11/2008 | Hageman et al. |
| 2009/0027466 | A1 | 1/2009 | Patel |
| 2011/0207663 | A1 | 8/2011 | Okunieff et al. |

FOREIGN PATENT DOCUMENTS

WO    WO9310758 A1    6/1993

OTHER PUBLICATIONS

Amit, M., Carpenter, M. K., Inokuma, M. S., Chiu, C. P., Harris, C. P., Waknitz, M. A., Itskovitz-Eldor, J., and Thomson, J. A. (2000) "Clonally derived human embryonic stem cell lines maintain pluripotency and proliferative potential for prolonged periods of culture", Dev Biol. 2, 271-78.

Bendall, S.C., Stewart, M.H., Menendez, P., George, D., Vijayaragavan, K., Werbowetski-Ogilvie, T., Ramos-Mejia, V., Rouleau, A., Yang, J., Bossé, M., Lajoie, G., and Bhatia, M. (2007) "IGF and FGF cooperatively establish the regulatory stem cell niche of pluripotent human cells in vitro", Nature 448, 1015-21.

Ciccolini, F., and Svendsen, C.N. (1998) "Fibroblast growth factor 2 (FGF-2) promotes acquisition of epidermal growth factor (EGF) responsiveness in mouse striatal precursor cells: identification of neural precursors responding to both EGF and FGF-2", J Neurosci. 19, 7869-80.

Cowan CA, Klimanskaya I, McMahon J, Atienza J, Witmyer J, Zucker JP, Wang S, Morton CC, McMahon AP, Powers D, Melton DA. (2004) "Derivation of embryonic stem-cell lines from human blastocysts", N Engl J Med. 350, 1353-6.

Ding, V., Choo, A.B., Oh, S.K. (2006) "Deciphering the importance of three key media components in human embryonic stem cell cultures", Biotechnol Lett. 7, 491-95.

Fasano CA, Dimos JT, Ivanova NB, Lowry N, Lemischka IR, Temple S. (2007) "shRNA knockdown of Bmi-1 reveals a critical role for p21-Rb pathway in NSC self-renewal during development", Cell Stem Cell 1, 87-99.

(Continued)

Primary Examiner — Karen Cochrane Carlson
Assistant Examiner — Natalie Moss
(74) Attorney, Agent, or Firm — Fish & Richardson P.C.

(57) ABSTRACT

Methods for culturing undifferentiated mammalian cells, such as stem and progenitor cells, are provided. The methods involve incubating the cell in the presence of a sustained release composition containing at least one growth factor, wherein the sustained release composition continuously releases the growth factor(s), and wherein the presence of the sustained level of growth factor maintains the cell in an undifferentiated state.

18 Claims, 14 Drawing Sheets

(56) References Cited

OTHER PUBLICATIONS

Fasano CA, Chambers SM, Lee G, Tomishima MJ, Studer L. (2010) "Efficient derivation of functional floor plate tissue from human embryonic stem cells", Cell Stem Cell 6, 336-47.

Itskovitz-Eldor, J., Schuldiner, M., Karsenti, D., Eden, A., Yanuka, O., Amit, M., Soreq, H., and Benvenisty, N. (2000) "Differentiation of human embryonic stem cells into embryoid bodies compromising the three embryonic germ layers", Mol Med. 2, 88-95.

Kilpatrick, T.J., and Bartlett, R.F. (1995) "Cloned multipotential precursors from the mouse cerebrum require FGF-2, whereas glial restricted precursors are stimulated with either FGF-2 or EGF", J Neurosci. 5, 3653-61.

Levenstein, M.E., Ludwig, T.E., Xu, R.H., Lianas, R.A., VanDenHeuvel-Kramer, K, Manning, D., and Thomson, J.A. (2006) "Basic fibroblast growth factor support of human embryonic stem cell self-renewal", Stem Cells 3, 568-74.

Ludwig, T.E., Bergendahl, V., Levenstein, M.E., Yu, J., Probasco, M.D., and Thomson, J.A. (2006) "Feeder-independent culture of human embryonic stem cells", Nat Methods. 8, 637-46.

Qian, X. Davis, A.A. Goderie, S.K., Temple, S. (1997) "FGF2 concentration regulates the generation of neurons and glia from multipotent cortical stem cells", Neuron 1, 81-83.

Raballo R, Rhee J, Lyn-Cook R, Leckman JF, Schwartz ML, Vaccarino FM. (2000) "Basic fibroblast growth factor (FGF2) is necessary for cell proliferation and neurogenesis in the developing cerebral cortex", J Neurosci. 13, 5012-23.

Shen Q, Goderie SK, Jin L, Karanth N, Sun Y, Abramova N, Vincent P, Pumiglia K, Temple S. (2004) "Endothelial cells stimulate self-renewal and expand neurogenesis of neural stem cells", Science 304, 1338-40.

Temple, S., and Qian, X. (1995) "bFGF, neurotrophins, and the control or cortical neurogenesis", Neuron 2, 249-52.

Thomson JA, Itskovitz-Eldor J, Shapiro SS, Waknitz MA, Swiergiel JJ, Marshall VS, Jones JM. (1998) "Embryonic stem cell lines derived from human blastocysts", Science 28, 1145-47.

Vaccarino FM, Schwartz ML, Raballo R, Rhee J, Lyn-Cook R. (1999) "Fibroblast growth factor signaling regulates growth and morphogenesis at multiple steps during brain development", Curr Top Dev Biol. 46 179-00.

Vescovi, A.L., Reynolds, B.A., Fraser, D.D., and Weiss, S. (1993) "bFGF regulates the proliferative fate of unipotent (neuronal) and bipotent (neuronal/astroglial) EGF-generated CNS progenitor cell", Neuron 5, 951-56.

Xu, C., Inokuma, M. S., Denham, J., Golds, K., Kundu, P., Gold, J. D., and Carpenter, M. K. (2001) "Feeder-free growth of undifferentiated human embryonic stem cells", Nat Biotechnol. 10, 971-74.

Xu, R.H., et al., "Basic FGF and suppression of BMP signaling sustain undifferentiated proliferation of human ES cells"; Nature Methods, 2(3):185-190 (Mar. 2005).

Zhu, G. et al.; "Stabilization of proteins encapsulated in injectable poly (lactide-co-glycolide)"; Nature Biotechnology; 18:52-57 (2000).

Piantino et al.; "An injectable, biodegradable hydrogel for trophic factor delivery enhances axonal rewiring and improves performance after spinal cord injury"; Experimental Neurology; 201(2):359-67 (2006).

Caldwell, M. et al. (2004) "Heparin stabilizes FGF-2 and modulates striatal precursor cell behavior in response to EGF"; Exp Neurol; 188:405-420.

Temple S.; "Division and differentiation of isolated CNS blast cells in microculture"; Nature 340:471-473 (1989).

K. Derwent et al.; "Thermoresponsive Hydrogels as a new ocular drug delivery platform to the posterior segment of the eye"; 106:206-214 (2008).

Pons et al., "PCR Site-Directed Mutagenesis Using *Pyrococcus* sp GB-D Polymerase Coupled to a Rapid Screening Procedure"; Methods in Molecular Biology; vol. 67; pp. 209-218 (1997).

Kunkel; "Rapid and efficient site-specific mutagenesis without phenotypic selection" Proc. Natl. Acad. Sci. USA; vol. 82; pp. 488-492 (1985).

Fukuoka et al.; "Ligand Binding Sites on Guinea Pig C3aR: Point and Deletion Mutations in the Large Extracellular Loop and Vinicity"; Biochemical Biophysical Research Communications; 263: 357-360 (1999).

Kim and Maas; "Multiple Site Mutagenesis with High Targeting Efficiency in One Cloning Step"; BioTechniques; 28: 196-198 (2000).

Parikh and Guengerich; "Random Mutagenesis by Whole-Plasmid PCR Amplification"; BioTechniques; 24: 4 28-431 (1998).

Wang et al.; "Two-Stage PCR Protocol Allowing Introduction of Multiple Mutations, Deletions and Insertions Using QuikChangeTM Site-Directed Mutagenesis"; BioTechniques; 26: 680-682 (1999).

Ray and Nickoloff; "Site-Specific Mutagenesis of Almost Any Plasmide Using a PCR-Based Version of Unique Site Elimination"; BioTech. 13: 342-346 (1992).

Angag and Schutz,; "General Method for Site-Directed Mutagenesis"; Biotechniques; 30: 486-488 (2001).

Ogel and McPherson; "Efficient deletion mutagenesis by PCR"; Protein Engineer; vol. 5; No. 5; pp. 467-468 (1992).

Kirsch and Joly; "An improved PCR-mutagenesis strategy for two-site mutagenesis or sequence swapping between related genes"; Nucleic Acids Research; vol. 26; No. 7; pp. 1848-1850 (1998).

Beckervordersandforth et al, "In Vivo Fate Mapping and Expression Analysis Reveals Molecular Hallmarks of Prospectively Isolated Adult Neural Stem Cells", Cell Stem Cell (2010) 7:744-758.

Hutchison et al., "Multiple Mutant cDNAs from One Reaction Mixture Using Asymmetric Primers in PCR", BioTech. vol. 19, No. 4, pp. 556-559 (1995).

Wang and Wilkinson; "Site-Directed Mutagenesis of Large (13-kb) Plasmids in a Single-PCR Procedure"; Biotech. 29: 976-978 (2000).

Xu et al., "Rapid PCR Method for Site-Directed Mutagenesis on Double-Stranded Plasmid DNA", Bio Techniques, vol. 20, No. 1, pp. 44-46 (1996).

Xu and Gong, "Adaptation of Inverse PCR to Generate an Internal Deletion", BioTech. 26: 639-641 (1999).

Takahashi, K. et al. "Induction of Pluripotent Stem Cells from Adult Human Fibroblasts by Defined Factors", Cell 131, 861-872 (2007).

Rhem and Hancock; "Membrane Topology of the Outer Membrane Protein OprH from *Pseudomonas aeruginosa*: PCR-Mediated Site-Directed Insertion and Deletion Mutagenesis"; Journal of Bacteriology; 178: 3346-3349 (1996).

Boles and Miogsa, "A rapid and highly efficient method for PCR-based site-directed mutagenesis using only one new primer", Curr. Genet. 28: 197-198 (1995).

Barrenttino et al., "Improved method for PCR-mediated site-directed mutagennesis", Nuc. Acids. Res. vol. 22, No. 3, pp. 541-542 (1994).

Tessier and Thomas, "PCR-Assisted Mutagenesis for Site-Directed Insertion/Deletion of Large DNA Segments", Methods in Molecular Biology 57, pp. 229-237.

De, S. et al., "Human Retinal Pigment Epithelium Cell Changes and Expression of aB-Crystallin", Arch Ophthalmol.; 125:641-646 (2007).

Maminishkis, A. et al., "Confluent Monolayers of Cultured Human Fetal Retinal Pigment Epithelium Exhibit Morphology and Physiology of Native Tissue", Invest Ophthalmol Vis Sci 47, 3612 (2006).

Burke, C. M. et al., "Phenotypic Heterogeneity of Retinal Pigment Epithelial Cells in Vitro and in Situ"; Exp Eye Res 62, 63 (1996).

Fasano et al., "Bmi-1 cooperates with Foxg1 to maintain neural stem cell self-renewal in the forebrain", Genes Dev.; 23; 561-74 (2009).

Bentolila et al., "Poly(N-acryl amino acids): A New Class of Biologically Active Polyanions", J. Med. Chem., 43 (13), pp. 2591-2600 (2000).

Lotz et al., "Sustained Levels of FGF2 Maintain Undifferentiated Stem Cell Cultures with Biweekly Feeding", 8(2) PloS One e56289 (Feb. 20, 2013).

Sahoo et al., "A bFGF-releasing silk/PLGA-based biohybrid scaffold for ligament/tendon tissue engineering using mesenchymal progenitor cells" Biomaterials, 31:2990-2998 (Jan. 25, 2010).

Okita et al, "Generation of germline-competent induced pluripotent stem cells"; Nature 448: 313-317 (2007).

Pittenger et al.; "Multilineage Potential of Adult Human Mesenchymal Stem Cells"; Science 284;143-7 (1999).

(56) References Cited

OTHER PUBLICATIONS

Herzog et al., "Plasticity of marrow-derived stem cells", Blood;102;3483-93 (2003).
Xu et al; "Immunosuppressive properties of cloned bone marrow mesenchumal stem cells"; Cell Research; 17;240-248 (2007).
Simmons and Torok-Storb; "Identification of stromal cell procursors in human bone marrow by a novel monoclonal antibody, STRO-1"; Blood; 78:55-62 (1991).
Govender et al., "PLGA nanoparticles prepared by nanoprecipitation: drug loading and release studies of a water soluble drug", Journal of Controlled Release; 57, pp. 171-185 (1999).
Mu, L. and Feng, S.; "A novel controlled release formulation for the anticancer drug paclitaxel (Taxol): PLGA nanoparticles containing vitamin E TPGS", J. of Controlled Release; 86, 33-48 (2003).
Bonnet and Dick; "Human acute myeloid leukemia is organized as a hierarchy that originates from a primitive hematopoietic cell", Nature Medicine (1997) vol. 3, No. 7, pp. 730-737.
Reya et al.; "Stem cells, cancer, and cancer stem cells"; 414:105-111 (2001).
Kai et al., "Breast Cancer Stem Cells", Breast cancer;17:80-85 (2010).
Gibson et al.; "Subtypes of medulloblastoma have distinct developmental origins", Nature; 468:1095-9 (2009).
Caccia et al., "Stabilization of recombinant human basic fibroblast growth factor by chemical modifications of cysteine residues", European Journal of Biochemistry, 204: 649-655 (1992).
Ashton, et al. "Scaffolds based on degradable alginate hydrogels and poly(lactide-co-glycolide) microspheres for stem cell culture", Biomaterials, 28, (2007) pp. 5518-5525.
Ya-Ping Li, et al.; "PEGylated PLGA nanoparticles as protein carriers: synthesis, preparation and biodistribution in rats"; Journal of Controlled Release, 71; pp. 203-211 (2001).
Simmons, C. A. et al.; "Dual growth factor delivery and controlled scaffold degradation enhance in vivo bone formation by transplanted bone marrow stromal cells"; Bone; 35:562-569 (2004).
Zhu, G. et al.; Stabilization of proteins encapsulated in injectable poly (lactide-co-glycolide); Nature Biotechnology; 18:52-57 (2000).
Henderson, J.K. et al., "Preimplantation Human Embryos and Embryonic Stem Cells Show Comparable Expression of Stage-Specific Embryonic Antigens", Stem Cells; 20(4):329-37 (2002).
Abramova et al, "Stage-specific changes in gene expression in acutely isolated mouse CNS progenitor cells", Developmental Biology 2005 283:269-81.
Shoemaker et al.; "Identification of Differentially Expressed Proteins in Murine Embryonic and Postnatal Cortical Neural Progenitors"; Plos One; vol. 5; issue 2; ppe9121 (2010).
Lowry, W.E., et al., "Generation of human induced pluripotent stem cells from dermal fibroblasts", Proc. Natl. Acad. Sci. USA 105, 2883-2888 (2008).
Maherali, N., et al., "Directly Reprogrammed Fibroblasts Show Global Epigenetic Remodeling and Widespread Tissue Contribution", Cell Stem Cell; 1, 55-70 (2007).
Park, et al.; "Reprogramming of human somatic cells to pluripotency with defined factors"; Nature 451, 141-146 (2008).
Takahashi, K, and Yamanaka, S.; "Induction of Pluripotent Stem Cells from Mouse Emryonic and Adult Fibroblast Cultures by Defined Factors"; Cell; 126, 663-676 (2006).
Takahashi, K. et al.; "Induction of Pluripotent Stem Cells from Adult Human Fibroblasts by Defined Factors"; Cell 131, 861-872 (2007).
Yu, J. et al.; "Induced Pluripotent Stem Cell Lines Derived from Human Somatic Cells"; Science; 318, 1917-1920 (2007).
Stadtfeld and Hochedlinger; "Induced pluripotency: history, mechanisms, and applications"' Genes Dev; 24:2239-2263 (2010).
Hochedliner and Plath, "Epigenetic reprogramming and induced pluripotency", 136;509-523 (2009).
Zhao et al.; "Process and formulation variables in the preparation of injectable and biodegradable magnetic microspheres"; BioMagnetic Research and Technology; 5:2 (2007).
Lu et al., "Isolation and characterization of human umbilical cord mesenchymal stem cells with hematopoiesis-supportive function and other potentials", Haematologica, 91: 1017-26 (2006).
Zeddou et al.; "The umbilical cord matrix is a better source of mesenchymal stem cells (MSC) than the umbilical cord blood"; Cell Biol. Int; vol. 34:693-701 (2010).
Lee et al. "Characterization of Expression Analysis of Mesenchymal Stem Cells from Human Bone Marrow and Adipose Tissue", Cell Physiol Biochem, 14:311-324 (2004).
Rosenbaum et al; "The use of mesenchymal stem cells in tissue engineering"; Organogenesis 4:23-27 (2008).
Lee et al, "Tumor stem cells derived from clioblastomas cultured in bFGF and EGF more closely mirror the phenotype and genotype of primary tumors than do serum-cultured cell lines", Cancer Cell, vol. 9 391-403 (2006).
Ricci-Vitiani et al; "Identification and expansion of human colon-cancer-initiating cells"; Nature; 445 pp. 111-115 (2007).
New, Bonnjie A.; and Yeoman, Lynn C; "Identification of Basic Fibroblast Growth Factor Sensitivity and Receptor and Ligand Expression in Human Colon Tumor Cell Lines", Journal of Cellular Physiology, 150:320-326 (1992).
Hawley et al; "Hematopoietic Stem Cells", Methods Enzymol; vol. 419; pp. 149-179 (2006).
Challen et al, "Mouse Hematopoietic Stem Cell Identification and Analysis", Cytometry A; 75(1): 14-24 (2009).
Edlund et al., "Degradable Polymer Microspheres for Controlled Drug Delivery", Advances in Polymer Science vol. 157, (2002).
Maherali and Hochedlinger, "Guidelines and Techniques for the Generation of Induced Pluripotent Stem Cells", Cell Stem Cell, 3:595-605 (2008).
Sotiropoulou PA, et al.; "Characterization of the Optimal Culture Conditions for Clinical Scale Production of Human Mesenchymal Stem Cells"; Stem Cells;24(2):462-71 (2006).
Cao, L. et al. "Sphere-forming cell subpopulations with cancer stem cell properties in human hepatoma cell lines", BMC Gastroenterol. Jun. 14, 2011;11(1):71.
Wakimoto et al.; "Human Glioblastoma-Derived Cancer Stem Cells: Establishment of Invasive Glioma Models and Treatment with Oncolytic Herpes Simplex Virus Vectors"; Cancer Research; 69(8):3472-81 (2009).
Lowry et al., "Multipotent embryonic spinal cord stem cells expanded by endothelial factors and Shh/RA promote functional recovery after spinal cord injury", Exp Neurol.; 209(2):510-22 (2008).
Yan J. et al., "Extensive Neuronal Differentiation of Human Neural Stem Cell Grafts in Adult Rat Spinal Cord"; PLoS Medicine; 4(2):e39; (2007).
Yeoh et al.; "Fibroblast Growth Factor-1 and -2 Preserve Long-Term Repopulating Ability of Hematopoietic Stem Cells in Serum-Free Cultures"; Stem Cells; 24:1564-1572 (2006).
Drury, J. L. et al., "Hydrogels for tissue engineering: scaffold design variables and applications", Biomaterials; 24:4337-4351 (2003).
Moioli et al "Sustained release of TGFbeta3 from PLGA microspheres and its effect on early osteogenic differentiation of human mesenchymal stem cells," Tissue Engineering, 12(3):537-546 (2006).
Tardieu et al., "Derivatized dextrans mimic heparin as stabilizers, potentiators, and protectors of acidic or basic FGF" Journal of Cellular Physiology, vol. 150, No .1, pp. 194-203, abstract, Jan. 1992.
Aubert-Pouessel et al., "A novel in vitro delivery system for assessing the biological integrity of protein upon release from PLGA microspheres," Pharmaceutical Research, vol. 19, No. 7, pp. 1046-1051 (Jul. 2002).
Lee et al., "New culture system for human embryonic stem cells: Autologous mesenchyal stem cell feeder without exogenous fibroblast growth factor 2", Differentiation 83:92-100 (2012).

* cited by examiner

Daily Media Change – Soluble FGF2

Twice per Week Media Change – FGF2-microspheres ered Jul. 1, 2010, which is herein incorporated by

SEQUENCE LISTING

```
<160> NUMBER OF SEQ ID NOS: 4

<210> SEQ ID NO 1
<211> LENGTH: 288
<212> TYPE: PRT
<213> ORGANISM: Homo sapiens
<300> PUBLICATION INFORMATION:
<308> DATABASE ACCESSION NUMBER: Genbank Accession Number NP_001997
```

<400> SEQUENCE: 1

```
Met Val Gly Val Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285
```

<210> SEQ ID NO 2
<211> LENGTH: 6774
<212> TYPE: DNA
<213> ORGANISM: Homo sapiens
<300> PUBLICATION INFORMATION:
<308> DATABASE ACCESSION NUMBER: Genbank Accession Number NM_002006

<400> SEQUENCE: 2

```
cggccccaga aaacccgagc gagtaggggg cggcgcgcag gagggaggag aactgggggc    60
gcgggaggct ggtgggtgtg gggggtggag atgtagaaga tgtgacgccg cggcccggcg   120
ggtgccagat tagcggacgc ggtgcccgcg gttgcaacgg gatcccgggc gctgcagctt   180
gggaggcggc tctccccagg cggcgtccgc ggagacaccc atccgtgaac cccaggtccc   240
gggccgccgg ctcgccgcgc accaggggcc ggcggacaga agagcggccg agcggctcga   300
ggctggggga ccgcgggcgc ggccgcgcgc tgccggggcgg gaggctgggg ggccggggcc   360
ggggccgtgc cccggagcgg gtcggaggcc ggggccgggg ccgggggacg gcggctcccc   420
```

```
gcgcggctcc agcggctcgg ggatcccggc cgggccccgc agggaccatg gcagccggga    480
gcatcaccac gctgcccgcc ttgcccgagg atggcggcag cggcgccttc ccgcccggcc    540
acttcaagga ccccaagcgg ctgtactgca aaacgggg cttcttcctg cgcatccacc     600
ccgacggccg agttgacggg gtccgggaga agagcgaccc tcacatcaag ctacaacttc    660
aagcagaaga gagaggagtt gtgtctatca aaggagtgtg tgctaaccgt tacctggcta    720
tgaaggaaga tggaagatta ctggcttcta aatgtgttac ggatgagtgt ttcttttttg    780
aacgattgga atctaataac tacaatactt accggtcaag gaaatacacc agttggtatg    840
tggcactgaa acgaactggg cagtataaac ttggatccaa acaggacct gggcagaaag     900 ctatacttt tcttccaatg tctgctaaga gctgatttta atggccacat ctaatctcat     960
ttcacatgaa agaagaagta tattttagaa atttgttaat gagagtaaaa gaaaataaat   1020
gtgtatagct cagtttggat aattggtcaa acaattttt atccagtagt aaaatatgta    1080
accattgtcc cagtaaagaa aaataacaaa agttgtaaaa tgtatattct ccctttata    1140 ttgcatctgc tgttacccag tgaagcttac ctagagcaat gatctttttc acgcatttgc   1200
tttattcgaa aagaggcttt taaaatgtgc atgtttagaa acaaaattc ttcatggaaa    1260 tcatatacat tagaaaatca cagtcagatg tttaatcaat ccaaaatgtc cactatttct   1320
tatgtcattc gttagtctac atgtttctaa acatataaat gtgaatttaa tcaattcctt   1380
tcatagtttt ataattctct ggcagttcct tatgatagag tttataaaac agtcctgtgt   1440
aaactgctgg aagttcttcc acagtcaggt caattttgtc aaacccttct ctgtacccat   1500
acagcagcag cctagcaact ctgctggtga tgggagttgt atttttcagtc ttcgccaggt   1560 cattgagatc catccactca catcttaagc attcttcctg gcaaaaattt atggtgaatg    1620
aatatggctt taggcggcag atgatataca tatctgactt cccaaaagct ccaggatttg    1680
tgtgctgttg ccgaatactc aggacggacc tgaattctga ttttatacca gtctcttcaa   1740
aaacttctcg aaccgctgtg tctcctacgt aaaaaaagag atgtacaaat caataataat   1800
tacactttta gaaactgtat catcaaagat tttcagttaa agtagcatta tgtaaaggct   1860
caaaacatta ccctaacaaa gtaaagtttt caatacaaat tctttgcctt gtggatatca   1920
agaaatccca aaatatttc ttaccactgt aaattcaaga agcttttgaa atgctgaata    1980
tttctttggc tgctacttgg aggcttatct acctgtacat ttttgggtc agctcttttt    2040 aacttcttgc tgctctttt cccaaaaggt aaaaatatag attgaaaagt taaaacattt    2100
tgcatggctg cagttccttt gtttcttgag ataagattcc aaagaactta gattcatttc   2160
ttcaacaccg aaatgctgga ggtgtttgat cagttttcaa gaaacttgga atataaataa    2220
ttttataatt caacaaaggt tttcacattt tataaggttg attttcaat taaatgcaaa    2280 tttgtgtggc aggatttta ttgccattaa catattttg tggctgcttt tctacacat      2340 ccagatggtc cctctaactg ggctttctct aattttgtga tgttctgtca ttgtctccca   2400
aagtatttag gagaagccct ttaaaaagct gccttcctct accactttgc tggaaagctt   2460
cacaattgtc acagacaaag attttttgttc caatactcgt tttgcctcta tttttcttgt   2520
ttgtcaaata gtaaatgata tttgcccttg cagtaattct actggtgaaa acatgcaaa    2580 gaagaggaag tcacagaaac atgtctcaat tcccatgtgc tgtgactgta gactgtctta   2640
ccatagactg tcttacccat cccctggata tgctcttgtt ttttccctct aatagctatg    2700
gaaagatgca tagaaagagt ataatgtttt aaaacataag gcattcgtct gccatttttc   2760
```

```
aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt ttccttaata agaaagtaa tttttactct gatgtgcaat     3180
acatttgtta ttaaatttat tatttaagat ggtagcacta gtcttaaatt gtataaaata    3240 tccctaaca tgtttaaatg tccatttta ttcattatgc tttgaaaaat aattatgggg      3300
aaatacatgt ttgttattaa atttattatt aaagatagta gcactagtct taaatttgat    3360
ataacatctc ctaacttgtt taaatgtcca tttttattct ttatgtttga aaataaatta    3420 tgggatcct atttagctct tagtaccact aatcaaaagt tcggcatgta gctcatgatc     3480
tatgctgttt ctatgtcgtg aagcaccgg atggggtag tgagcaaatc tgccctgctc      3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720
tgaaattttt aatcaagata gtgtgcttta ttctgttgta ttttttatta ttttaatata    3780
ctgtaagcca aactgaaata acatttgctg ttttataggt ttgaagaaca taggaaaaac    3840
taagaggttt tgttttattt tttgctgatg aagagatatg tttaaatatg ttgtattgtt    3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgattttt     4140 aagaaggcag tttgtcaatt ttaatcttgt ggatacctt atactcttag ggtattattt      4200
tatacaaaag ccttgaggat tgcattctat tttctatatg accctcttga tatttaaaaa    4260
acactatgga taacaattct tcatttacct agtattatga agaatgaag gagttcaaac      4320 aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt ttcatttcta    4560
gctgctttca gggttttatg aattttcagg caaagcttta atttatacta agcttaggaa    4620
gtatggctaa tgccaacggc agttttttc ttcttaattc cacatgactg aggcatatat     4680
gatctctggg taggtgagtt gttgtgacaa ccacaagcac tttttttttt tttaagaaa     4740 aaaaggtagt gaattttaa tcatctggac tttaagaagg attctggagt atacttaggc     4800
ctgaaattat atatatttgg cttggaaatg tgttttctt caattacatc tacaagtaag     4860
tacagctgaa attcagagga cccataagag ttcacatgaa aaaatcaat ttatttgaaa     4920 aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
acaccactac aaaatcatct tttatatcaa cagaagaata agcataaact aagcaaaagg    5160
```

-continued

```
tcaataagta cctgaaacca agattggcta gagatatatc ttaatgcaat ccattttctg    5220
atggattgtt acgagttggc tatataatgt atgtatggta ttttgatttg tgtaaaagtt    5280
ttaaaaatca agctttaagt acatggacat ttttaaataa aatatttaaa gacaatttag    5340
aaaattgcct taatatcatt gttggctaaa tagaataggg acatgcata ttaaggaaaa     5400 ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttattttata tttccttgtc ttaaatactg    5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat ttgttttctc atagtttaat    5820
tccaacaaca atattagtcg tatccaaaat aaccttaat gctaaacttt actgatgtat      5880
atccaaagct tctcattttc agacagatta atccagaagc agtcataaac agaagaatag    5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
attggaaaat ttaaattttt attcttagct ataaagcaag aaagtaaaca cattaatttc    6120
ctcaacattt ttaagccaat taaaaatata aaagatacac accaatatct tcttcaggct    6180
ctgacaggcc tcctggaaac ttccacatat ttttcaactg cagtataaag tcagaaaata    6240
aagttaacat aactttcact aacacacaca tatgtagatt tcacaaaatc cacctataat    6300
tggtcaaagt ggttgagaat atattttta gtaattgcat gcaaaatttt tctagcttcc     6360
atcctttctc cctcgtttct tctttttttg ggggagctgg taactgatga aatcttttcc    6420
caccttttct cttcaggaaa tataagtggt tttgtttggt taacgtgata cattctgtat    6480
gaatgaaaca ttggagggaa acatctactg aatttctgta atttaaaata ttttgctgct    6540
agttaactat gaacagatag aagaatctta cagatgctgc tataaataag tagaaaatat    6600
aaatttcatc actaaaatat gctatttaa atctatttc ctatattgta tttctaatca     6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 3
<211> LENGTH: 105
<212> TYPE: PRT
<213> ORGANISM: Mus musculus
<300> PUBLICATION INFORMATION:
<308> DATABASE ACCESSION NUMBER: Genbank Accession Number AAP92385

<400> SEQUENCE: 3

```
Gly Val Arg Glu Lys Ser Asp Pro His Val Lys Leu Gln Leu Gln Ala
  1               5                  10                  15

Glu Glu Arg Gly Val Val Ser Ile Lys Gly Val Cys Ala Asn Arg Tyr
             20                  25                  30

Leu Ala Met Lys Glu Asp Gly Arg Leu Leu Ala Ser Lys Cys Val Thr
         35                  40                  45

Glu Glu Cys Phe Phe Phe Glu Arg Leu Glu Ser Asn Asn Tyr Asn Thr
     50                  55                  60

Tyr Arg Ser Arg Lys Tyr Ser Ser Trp Tyr Val Ala Leu Lys Arg Thr
 65                  70                  75                  80
```

```
Gly Gln Tyr Lys Leu Gly Ser Lys Thr Gly Pro Gly Gln Lys Ala Ile
                85                  90                  95

Leu Phe Leu Pro Met Ala Ser Lys Ser
            100                 105

<210> SEQ ID NO 4
<211> LENGTH: 695
<212> TYPE: DNA
<213> ORGANISM: Mus musculus
<300> PUBLICATION INFORMATION:
<308> DATABASE ACCESSION NUMBER: Genbank Accession Number NM_008006

<400> SEQUENCE: 4
ggccccgggc cgttgtacac tcaaggggct ctctcggctt caggaagagt ccggctgcac      60
tgggctggga gcccggcggg acacggactg ggaggctggc agcccgcggg cgagccgcgc     120 tgggggggccg aggccggggt cggggccggg gagccccaag agctgccaca gcggggtccc    180
ggggccgcgc aagggccatg gctgccagcg gcatcacctc gcttcccgca ctgccggagg    240
acggcggcgc cgccttccca ccaggccact tcaaggaccc caagcggctc tactgcaaga    300
acggcggctt cttcctgcgc atccatcccg acggccgcgt ggatgcgtc cgcgagaaga    360 gcgacccaca cgtcaaacta caactccaag cagaagagag aggagttgtg tctatcaagg    420
gagtgtgtgc caaccggtac cttgctatga aggaagatgg acggctgctg gcttctaagt    480
gtgttacaga agagtgtttc ttctttgaac gactggaatc taataactac aatacttacc    540
ggtcacggaa atactccagt tggtatgtgg cactgaaacg aactgggcag tataaactcg    600
gatccaaaac gggacctgga cagaaggcca tactgtttct tccaatgtct gctaagagct    660
gactcacttt tgacactgtc actgagacac tgtca                                695
```

METHODS FOR CULTURING UNDIFFERENTIATED CELLS USING SUSTAINED RELEASE COMPOSITIONS

RELATED APPLICATIONS

The present application is a continuation of U.S. patent application Ser. No. 13/175,667, which was filed on Jul. 1, 2011 and issued, on Jul. 9, 2013, as U.S. Pat. No. 8,481,308. Said U.S. patent application Ser. No. 13/175,667 claims the benefit of U.S. Provisional Patent Application Ser. No. 61/360,741, filed Jul. 1, 2010, which is herein incorporated by reference in its entirety.

REFERENCE TO SEQUENCE LISTING

This specification includes a sequence listing which was submitted to the United States Patent and Trademark Office on Aug. 27, 2013 as an ASCII compliant text file named "SeqListing.txt" that was created on Aug. 21, 2013 and has a size of 13,046 bytes. The contents of the aforementioned file named "SequenceListing.txt" are hereby incorporated by reference in their entirety.

TECHNICAL FIELD

The present invention provides improved methods for culturing undifferentiated mammalian cells, such as stem and progenitor cells. The methods involve incubating the cell in the presence of a sustained level of at least one growth factor. A sustained release composition that continuously releases the growth factor is used to maintain sustained levels of the growth factor, and wherein the presence of the sustained levels of growth factor maintains the cell in an undifferentiated state and increases the quantity and/or quality of cells produced.

BACKGROUND OF THE INVENTION

Stem cells are undifferentiated cells that possess two hallmark properties; self-renewal and the ability to differentiate into one or more different cell lineages. The process of self-renewal involves the self-replication of a stem cell to allow for propagation and expansion, wherein the stem cell remains in an undifferentiated state. Progenitor cells are also undifferentiated cells that have the ability to differentiate into one or more cell lineages, but have limited or no ability to self renew. When maintained in culture, undifferentiated cells, such as stem or progenitor cells, can undergo spontaneous differentiation, thereby losing the desired, undifferentiated cell phenotype. Thus, culture methods that minimize spontaneous differentiation in order to maintain the undifferentiated stem or progenitor cell state are needed.

Keeping undifferentiated cells, such as, but not limited to, stem and/or progenitor cells in an undifferentiated state is critical to their use, e.g., in industry and medicine, since a major scientific and therapeutic usefulness of these cells lies in their ability to expand into homogenous populations that can further proliferate or differentiate into mature cells as needed, e.g., for scientific study or to repair damage to cells or tissues of a patient. Once they have spontaneously differentiated in cell culture, the cells are less proliferative and less able to differentiate into different types of cells as needed. A homogenous culture of undifferentiated stem cells is therefore a highly sought after but unrealized goal of research scientists and industry.

Current methods for culturing undifferentiated cells (e.g., various types of stem cells) attempt to minimize such spontaneous differentiation by delivering fibroblast growth factor 2 (FGF2) to the cell cultures daily, or, less frequently than every day, which is known as "feeding". FGF2 has been shown to promote self-renewal of stem cells by inhibiting differentiation of the stem cell; however this inhibition is incomplete, and the stem cell cultures tend to gradually differentiate, thereby diminishing usefulness of the stem cell culture. Furthermore, stem cells, such as ES cells, typically need to be grown on mouse embryonic fibroblast (MEF) feeder cells. This is a cumbersome step that is desirable to remove.

For human embryonic stem cells (hESC), as well as other undifferentiated cell types, FGF2 is required for the maintenance of the undifferentiated state, and withdrawal of FGF2 from the culture conditions initiates differentiation. [See, Amit, M., et al. (2000) Dev Biol. 2, 271-78; Itskovitz-Eldor, J., et al. (2000) Mol Med. 2, 88-95; Xu, C., et al. (2001) Nat Biotechnol. 10, 971-74; Xu et al., 2005; Xu, R. H., et al. (2005) 3, 164-65; Ding, V., et al. (2006) Biotechnol Lett. 7, 491-95; Levenstein, M. E., et al. (2006) Stem Cells 3, 568-74; Ludwig, T. E., et al. (2006) Nat Methods. 8, 637-46; Bendall, S. C., et al. Nature 448, 1015-21]. FGF2 is also required to maintain neural stem cells (NSC) and neural progenitor cells in an undifferentiated state. [See, Temple S. (1989). Nature 340:471-473.; Vescovi, A. L., et al. (1993) Neuron 5, 951-56; Kilpatrick, T. J., and Bartlett, P. F. (1995) J Neurosci. 5, 3653-61; Temple, S., and Qian, X. (1995) Neuron 2, 249-52; Qian, X., et al. (1997) Neuron 1, 81-83; Ciccolini, F., and Svendsen, C. N. (1998) J Neurosci. 19, 7869-80; Vaccarino F M, et al. (1999) Curr Top Dev Biol. 46 179-00; Raballo R, et al. J Neurosci. 13, 5012-23.] In traditional methods for culturing NSCs, growth factors such as FGF2 are only replenished once every three days. However, NSCs cultured by these methods are reported to have high rates of spontaneous differentiation [Qian et al., 1997, supra].

Growth factors, such as FGF2, are understood to work directly on hESCs, NSCs, and other stem and progenitor cells, and/or, in some methods, indirectly by stimulating feeder cells in the cell culture to produce this and other growth factors [Bendall, et al., 2007, supra]. However, levels of FGF2 and other growth factors are unstable in these cell cultures, and must be frequently replaced. For example, the half-life of FGF2 is less than 24 hours under conditions typically used to culture stem and progenitor cells. [McKinnon et al., 1990, Neuron. 1990 November; 5(5):603-14]. Consequently, standard methods for maintaining hESC cultures require feeding the cells every day with soluble FGF2 and/or other growth factors in order to maintain effective amounts of active FGF2 polypeptide and/or those other growth factors [Fasano C A, et al. (2010) Cell Stem Cell 6, 336-47]. Despite that laborious, time-consuming process, however, daily feeding of FGF2 and/or other growth factors to stem and progenitor cells still results in (1) significant variation of growth factor levels, with very high levels of FGF2 for the few hours immediately after feeding and very low FGF2 levels present during the few hours prior to the next daily feeding, and (2) limited effectiveness, since hESCs still gradually differentiate, albeit at a slower rate than in the absence of daily feeding with FGF2.

Biodegradeable "microspheres" and "millicylinders" prepared from biocompatible polyesters of glycolic and lactic acids ("PLGA") are known for delivering protein drugs to patients, and PLGA millicylinders encapsulated with recombinant human FGF2 (also known as "basic fibroblast growth factor" or "bFGF") have been described by Zhu et al. (*Nature Biotechnology* (2000) 18:52-57) for such applications. Olaye et al. (*European Cells and Materials* (2008) 16 (Suppl. 3):86) teach that "PLGA microspheres have been extensively used for the sustained delivery of growth factors for embryonic stem cell differentiation," and report that PLGA microsphere-based scaffolds were successfully used to deliver certain growth factors—specifically Asc, Dex and TGF-$\beta_1$—for differentiation of murine embryonic stem cells into osteoblast and chondrocyte-like cells. PVA-based polymer coatings and hydrogel particles for cell culturing have also been described, e.g., by Hemperly et al., U.S. Patent Application Publication No. 2004/0209361 and Keith et al., U.S. Patent Application Publication No. 2004/0209360, respectively. These polymer coatings and particles promote cell adhesion, and may also provide slow release of "bioaffecting molecules," such as growth factors. Id. More recent publications emphasize a role for FGF2 in promoting cellular differentiation, and discuss hydrogels, microspheres and the like for tissue specific delivery of that growth fact, e.g., to promote tissue regeneration and wound healing. For review, see Yun et al., *J. Tissue Eng.* (Nov. 7, 2010) 2010:218142; see also Macdonald et al., *Biomacromolecules* (Aug. 9, 2010) 11(8): 2053-2059. Hence, the use of such "sustained release" preparations in stem cell cultures has been limited to delivering growth factors for stem cell differentiation. The sustained release of growth factors, using such compositions or otherwise, for maintaining cells in an undifferentiated state is believed to be heretofore unknown. Hence, there remains a need in the art for improved methods of culturing stem cells and other undifferentiated cells, and for maintaining such cells in an undifferentiated state.

SUMMARY OF THE INVENTION

As follows from the Background Section, there is a clear need for compositions and methods for culturing undifferentiated cells, such as ESCs, NSCs, and other types of undifferentiated cells (e.g. RPESCs, iPSCs, SCSCs, etc.) that reduces or eliminates their spontaneous differentiation. There is also a need in the art for compositions and methods to reduce the time, labor and expense currently required for culturing undifferentiated cells. These and other problems which will be apparent to persons of ordinary skill in the art are at least partially solved by the present invention.

Thus, in one aspect, the present invention provides a method for culturing a mammalian stem or progenitor cell, wherein the method comprises incubating the stem or progenitor cell in the presence of a stable concentration range of at least one growth factor over a period of at least 1 day. In certain embodiments, the stable concentration range of growth factor is maintained by continuous release of the growth factor using mechanical means. In other embodiments, the stable concentration range of growth factor is maintained by a sustained release composition, such as a PLGA microsphere containing the growth factor.

In another aspect, the present invention provides a method for culturing a mammalian stem or progenitor cell, wherein the method comprises incubating the stem or progenitor cell in the presence of a sustained release composition containing at least one growth factor, wherein the sustained release composition releases the growth factor, and wherein the presence of the growth factor maintains the cell in an undifferentiated state. In certain embodiments, the released growth factor is maintained within a predetermined concentration range.

In another aspect, the present invention provides a method for culturing a stem or progenitor cell, wherein the method comprises incubating the stem or progenitor cell in the presence of a sustained release composition comprising fibroblast growth factor 2 (FGF2), wherein the sustained release composition releases FGF2. In certain embodiments, the sustained release composition comprises FGF2 at a concentration of 0.5% (w/v) at the start of incubation with the stem or progenitor cell. Furthermore, the released FGF2 is maintained within a predetermined concentration range.

In yet another aspect, the present invention provides a method for culturing an undifferentiated mammalian cell, wherein the method comprises incubating the undifferentiated mammalian cell in the presence of a sustained release composition containing at least one growth factor, wherein the sustained release composition releases the growth factor, wherein the released growth factor is maintained within a predetermined concentration range, and wherein the maintenance of the released growth factor within said concentration range maintains the cell in an undifferentiated state.

In any of the above methods for culturing the stem or progenitor cell or undifferentiated mammalian cell, the sustained release of the growth factor may maintain the concentration of the growth factor in the cell culture in a stable concentration range of 80%-100%, 80%-95%, or 80%-90% of the starting concentration of growth factor.

In any of the above methods for culturing the stem or progenitor cell or undifferentiated mammalian cell, the sustained release composition may release at least one growth factor over a period of over at least 1 day, at least 2 days, at least 3 days, at least 4 days, at least 5 days, at least 6 days, or at least 7 days, or longer, e.g., 2 weeks, 3 weeks, 4 weeks, 5 weeks, or longer.

In any of the above methods for culturing the stem or progenitor cell or undifferentiated mammalian cell, the cell may be maintained in an undifferentiated state for over at least 1 day, at least 2 days, at least 3 days, at least 4 days, at least 5 days, at least 6 days, or at least 7 days, or longer, e.g., 2 weeks, 3 weeks, 4 weeks, 5 weeks, or longer.

In any of the above methods for culturing the stem or progenitor cell or undifferentiated mammalian cell, the sustained release composition is a poly(DL-lactide-co-glycolide) (PLGA) microsphere. In certain embodiments, the concentration of the PLGA microsphere ranges from about 5 to about 300 ng/ml.

In any of the above methods for culturing the stem or progenitor cell or undifferentiated mammalian cell, the sustained release composition may further comprises one or more of heparin, dextran sulfate, $Mg(OH)_2$, a polyanion that complexes with growth factor, and/or EDTA. In certain embodiments, the sustained release composition further comprises 1.0% (w/v) heparin and/or 1.0% (w/v) dextran sulfate. In other embodiments, the ratio of heparin or dextran sulfate to FGF2 is about 2:1. In still other embodiments, the sustained release composition further comprises 3% (w/v) $Mg(OH)_2$. In yet other embodiments, the sustained release composition further comprises 1 mM EDTA.

In any of the above methods for culturing the stem or progenitor cell or undifferentiated mammalian cell, the stem cell is selected from the group consisting of an embryonic stem cell, an induced-pluripotent stem cell, a neural stem cell, a retinal pigment epithelial stem cell, a mesenchymal stem cell, a hematopoietic stem cell, an epiblast stem cell or a cancer stem cell. In certain embodiments, the stem cell is a human embryonic stem cell or a neural progenitor cell.

In any of the above methods for culturing the stem or progenitor cell or undifferentiated mammalian cell, the sustained release composition further comprises one or more additional growth factors. In certain embodiments, the one or more additional growth factors are selected from the group consisting of epidermal growth factor (EGF), platelet-derived growth factor (PDGF), sonic hedgehog (Shh), leukemia inhibitory factor (LIF) and a Wnt protein.

The details of one or more embodiments of the invention are set forth in the accompanying drawings and the description below. Other features, objects, and advantages of the invention will be apparent from the description and drawings, and from the claims.

DETAILED DESCRIPTION

I. Definitions

Figure 1A:
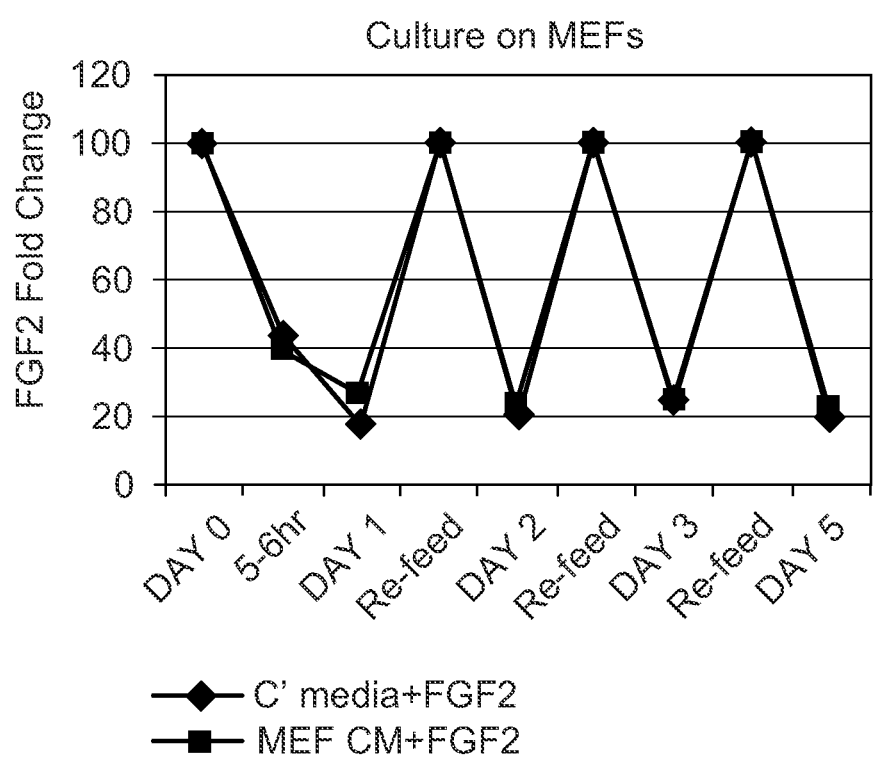
FIG. 1 contains graphs showing the percent (%) change in FGF2 concentrations 5-6 hours after culturing hESCs on mouse embryonic fibroblasts (MEFs) (FIG. 1A) or on Matrigel (non-MEF) (FIG. 1B) in complete hESC culture media containing 10 ng/ml FGF2 ("C' media+FGF2") or MEF conditioned media containing 10 ng/ml FGF2 ("MEF CM+FGF2") media relative to the concentration at the start of culture.

As used herein, the term "stem cell" refers to a cell that retains the ability to renew itself through mitotic cell division, and can differentiate into a diverse range of specialized cell types. The term "stem cell" includes by way of non-limiting examples, neural stem cells (NSCs), embryonic stem cells (ESCs), induced pluripotent stem cells (iPSCs), hematopoietic stem cells (HSCs), cancer stem cells (CSCs), spinal cord stem cells (CSCs), mesenchymal stem cells (MSCs), retinal pigment epithelial stem cells (RPESCs), and epiblast stem cells. As used herein, the term "embryonic stem cell (ESC)" refers to a stem cell derived from the inner cell mass of a blastocyst, an early-stage embryo. Human embryos reach the blastocyst stage 4-5 days post fertilization, at which time they consist of 50-150 cells.

The term "progenitor cell" as used herein refers to an undifferentiated cell that has the ability to proliferate and differentiate into one or more different cell lineages, but is thought to have no or limited ability to self renew. Typically, a stem cell culture, such as, e.g., an hESC culture or NSC culture, will contain some progenitor cells in addition to stem cells. In some instances, progenitor cells derive from stem cells, during the process losing the ability to self-renew but maintaining the ability to differentiate into one or more different cell lineages. In other words, stem cells can give rise to progenitor cells.

As used herein, the terms "neural stem cell" and "neural progenitor cell (NPC)" describes undifferentiated cells that can generate nervous system cells. NSCs have the ability to self renew, whereas NPCs are thought to have very limited or no ability to self renew.

As used herein, a "retinal pigment epithelial stem cell" ("RPESC") is a stem cell that is activated from the adult human retinal pigment epithelium (RPE).

As used herein, induced pluripotent stem cells ("iPSCs") are pluripotent stem cells expressing many of the genetic and phenotypic characteristics of ES cells, and are derived from differentiated (e.g., somatic). iPSCs have the same gross morphology as ES cells, proliferative properties, form teratomas after transplantation into nude mice, and have the ability to differentiate along all 3 germ layers in vitro. Their responses to key factors such as retinoic acid and leukemia inhibitory factor (LIF) are also the same as those observed for ES cells [see, Okita et al, 2007; Nature 448: 313-317].

As used herein, "mesenchymal stem cells (MSCs)" are multipotent stem cells that can be derived from a variety of tissues and can differentiate into a variety of cell types, including osteoblasts (bone cells), chondrocytes (cartilage cells) and adipocytes (fat cells) and are capable of self renewal [see, Pittinger et al. Science (1999) 284; 143-7; Herzog (2003) Blood; 102; 3483-93]. MSCs have been characterized by a number of surface markers including expression of markers from the following list: CD29, CD44, CD73, CD105, CD106, CD166 and STRO-1 [see, Xu et al; Cell Research (2007) 17; 240-248; Simmons and Torok-Storb (1991) Blood; 78:55-62].

Hematopoietic stem cells ("HSCs") are multipotent stem cells that give rise to all the blood cell types from the myeloid (monocytes and macrophages, neutrophils, basophils, eosinophils, erythrocytes, megakaryocytes/platelets, dendritic cells), and lymphoid lineages (T-cells, B-cells, NK-cells), and are capable of self renewal. Mouse and human HSCs have been identified by different combinations of markers. Mouse HSCs typically express c-Kit and Sca-1 but are negative for markers of mature hematopoietic cell lineages (Lin−) [see, Challen et al. Cytometry A; 2009; 75; 14-24]. Human HSCs have been described as CD34+ CD133+ Lin− cells [see, Hawley et al, 2006 Methods in Enzymol 419:149-179].

As used herein, a "cancer stem cell (CSC)" is a cancer cell (typically found within tumors or hematological cancers) that possesses the ability to give rise to all cell types found in a particular cancer sample and the ability to self renew. These cells are also termed 'tumor initiating cells', as these are recognized to have stem cell properties. Typically cancer stem cells share markers of stem cells of the tissue of origin, thus leukemia stem cells can be identified as CD34+ CD38− and breast cancer stem cells can be identified as CD24− CD44+ [see, Bonnet and Dick; Nature Medicine (1997) 3:730-737; Reya et al. (2001) 414:105-111; Kai et al. (2010) Breast cancer; 17:80-85; Gibson et al.; Nature; 2010; 468: 1095-9].

The term "growth factor" can be a naturally occurring, endogenous or exogenous protein, or recombinant protein, capable of inhibiting and/or stimulating differentiation of cells, such as e.g., stem or progenitor cells. The term "growth factor" also can encompass lipid, chemical, and other non-protein agents, e.g., small molecules that are capable of inhibiting and/or stimulating cell differentiation. In certain embodiments, the term "growth factor" refers to any polypeptide or other agent that is capable of inhibiting or stimulating cell differentiation, e.g., when present in effective amounts in a stem or progenitor cell culture. Growth factor polypeptides of the present invention include both naturally occurring and recombinant proteins, which may be either endogenous or exogenous to the cells being cultured. In addition, a growth factor of the invention may be a synthetic protein, such as a fusion or other protein construct or a chemical modification of the amino acid sequences derived from a naturally occurring growth factor or other protein. Such growth factors may be used in combination, to produce, e.g., an additive or synergistic effect, according to the present methods.

A preferred growth factor used in the present invention is known as "basic fibroblast growth factor (bFGF)" or, alternatively, as "fibroblast growth factor 2 (FGF2)." The terms bFGF and FGF2 are synonymous and refer to full-length proteins or any functionally active fragment thereof, which can be an isolated, naturally occurring form of FGF2 or a recombinant form. Active fragments, mutant forms and chemical modifications of FGF2 that retain the functional properties of wild-type FGF2 (specifically, the ability to maintain cells in an undifferentiated state), are contemplated for use in the methods of the present invention. Modifications of growth factor for the stabilization of the growth factor are described in detail, for example, in Caccia et al. (1992) European Journal of Biochemistry, 204: 649-655. Caccia et al. describe stabilized forms of recombinant human basic fibroblast growth factor by chemical modifications of cysteine residues. Formulations for stabilizing FGF2 are also described in U.S. Pat. No. 5,217,954 by Foster et al.

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation. Exemplary sequences of FGF2 polypeptides that may be used in the present invention are known in the art and are available, e.g., from the GenBank® database. For example, the amino acid sequence of an exemplary human FGF2 polypeptide is available under the GenBank® Accession No. NP_001997 (SEQ ID NO: 1), whereas the amino acid sequence of an exemplary mouse FGF2 polypeptide is available from GenBank® under the Accession No. AAP92385 (SEQ ID NO: 3). Sequences of exemplary nucleic acids encoding these human and mouse FGF2 polypeptide sequences are also available from GenBank®, under the Accession Nos. NM_002006 (SEQ ID NO: 2) and NM_008006 (SEQ ID NO: 4), respectively.

FGF2 polypeptides that may be used in the present invention may also be obtained from commercial sources, such as from, e.g., R&D Systems (Minneapolis, Minn.); Peprotech, (Rocky Hill, N.J.); Becton Dickinson, (San Jose, Calif.); Invitrogen, (Carlsbad, Calif.). Recombinant FGF2 may also be expressed in cells using any suitable expression system known in the art for producing recombinant protein. Recombinant and/or naturally occurring FGF2 can be isolated using any suitable technique known in the art.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein can be associated with other proteins or nucleic acids, or both, with which it associates in the cell, or with cellular membranes if it is a membrane-associated protein.

The terms "express" and "expression" mean allowing or causing the information in a gene or DNA sequence to become manifest, for example, producing an non-coding (untranslated) RNA or a protein by activating the cellular functions involved in transcription and translation of a corresponding gene or DNA sequence. A DNA sequence is expressed in or by a cell to form an "expression product" such as RNA or a protein. The expression product itself, e.g. the resulting RNA or protein, may also be said to be "expressed" by the cell. The term "expression system" means a host cell and compatible vector under suitable conditions, e.g. for the expression of a protein coded for by foreign DNA (the "expression construct") carried by the vector and introduced to the host cell. By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes. By "operatively associated with" is meant that a target nucleic acid sequence and one or more expression control sequences (e.g., promoters) are physically linked so as to permit expression of the polypeptide encoded by the target nucleic acid sequence within a host cell.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest. For example, FGF2 can be expressed using *E. coli* bacteria and does not need to be modified posttranslationally to be active. Any growth factors encompassed by the present invention can be expressed as recombinant protein, or isolated from a naturally occurring source, or purchased commercially, when available.

As used herein, the term "sustained release of a growth factor" from a sustained release composition, in the context of a cell culture, means the growth factor is released from the sustained release composition (i.e., is made available to the cells in the cell culture) over a period of time, preferably over at least 1 day, at least 2 days, at least 3 days, at least 4 days, at least 5 days, at least 6 days, or at least 7 days, or longer, e.g., 2 weeks, 3 weeks, 4 weeks, 5 weeks or longer, and the released growth factor is maintained at a constant concentration, or relatively constant concentration (i.e., a "stable concentration range"), in the cell culture. The stable concentration range is preferably within about 50% of the starting growth factor concentration. Hence, in the context a cell culture, the growth factor is preferably released from the sustained release composition such that the concentration or amount of growth factor available to the cells (preferably a period of at least 1-7 days, as set forth above) is within 50% of the amount or concentration of the growth factor that is available to the cells at the beginning of that time period. In even more preferable embodiments, the stable concentration range is not less than about 60%, 70%, 80%, 90% or 95% of the starting growth factor concentration. In particularly preferred embodiments, the concentration of released growth factor stays within the range of about 80%-100%, 80%-95%, or 80%-90% of the starting concentration of the growth factor over a period of 1 day or more. In other preferred embodiments, the concentration of released growth factor stays within the range of at least 80%-100%, 80%-95%, or 80%-90% of the starting concentration of the growth factor over a period of 3 days or more. Sustained release of a growth factor, such as FGF2, can be confirmed by detecting the levels of the growth factor in the cell culture over time (e.g., by ELISA). Sustained release of a growth factor may also be referred to herein as "time release" of the growth factor, or stabilization of the growth factor, and includes any means or method of maintaining a stable concentration range of released growth factor (e.g., in a cell culture).

A "sustained release composition" of the invention can include any suitable vehicle that results in the maintenance of a stable concentration range of one or more released factors (e.g., growth factors) over a period of time. As used herein, sustained release compositions are suitable for culturing with undifferentiated cells, such as but not limited to stem and/or progenitor cells. Non-limiting examples of sustained release compositions of the invention include microspheres (e.g., poly(DL-lactide-co-glycolide) (PLGA) microspheres), anhydrous poly-vinyl alcohol (PVA), millicylinders, alginate gels, biodegradable hydrogels, complexing agents and nanoparticles. [See, e.g., Ashton, et al. (2007) Biomaterials, 28, 36, 5518; Drury, J. L. et al. (2003) Biomaterials; 24:4337-4351; U.S. Pat. No. 7,226,617 to Ding et al.; Simmons, C. A. et al. (2004) Bone; 35:562-569; Zhu, G. et al. (2000) Nat Biotech; 18:52-57, Biodegradable Hydrogels for Drug Delivery, K. Park et al, 1993, Technomic Publishing, Trans Am Ophthalmol Soc, K. Derwent et al, 2008; 106:206-13.] Mechanical means and methods for time-release are also included, for example manual addition or a mechanical device (e.g. robotic) can be used to provide a continuous, or near continuous, sustained supply of growth factor to a cell culture over time and thereby maintain the stem or progenitor cells at a stable level of differentiation due to exposure to a stable concentration of growth factor. Modifications of the growth factor or other means to reduce degradation and thereby result in a sustained concentration range of growth factor exposed to the stem cell culture are also included.

As used herein, the term "maintains the cell in an undifferentiated state" refers to preventing or minimizing the amount of cell differentiation, e.g., spontaneous differentiation in culture. In certain embodiments, such as, e.g., when culturing stem or progenitor cells, the term also includes maintaining the immature state which increases the ability of the stem cell to differentiate into one or more mature, differentiated cell lineages. For example, a multipotent stem cell or progenitor cell that is maintained in an undifferentiated state will express markers associated with stem or progenitor cells, but will express no or low levels of markers associated with differentiating or differentiated cells, and will also maintain its ability to differentiate into one more different cell lineages, i.e., will remain multipotent. Thus, a unipotent keratinocyte progenitor cell that is maintained in the undifferentiated state, for example, will not differentiate into a keratinocyte (i.e., will remain a progenitor cell), but will maintain the ability to differentiate into a keratinocyte (e.g., under appropriate culture conditions that signal the cell to undergo such differentiation).

Generally, it is possible to determine if a stem or progenitor cell is "maintained" as a stem or progenitor cell (i.e., maintained in an undifferentiated state) by determining whether it continues to express one or more markers associated with such cells. For example, markers of human embryonic stem cells, include, but are not limited to the markers OCT4, NANOG, TRA-1-81, SOX2, SSEA-4, and/or SSEA-3. Markers of NSCs and NPCs include without limitation, Nestin, Lex (CD-15), Musashi, Bmi-1, Sox1, Hes1, Hes5, BLBP, and CD133. In addition, an ESC that is maintained in an undifferentiated state generally will not express, or will express relatively low levels of markers indicative of differentiation such as Brachyury, Sox17, Foxa2, Pax6, Otx2, and Sox1. An NSC that is maintained in an undifferentiated state will not express, or will express relatively low levels (compared to a differentiated cell) of markers including without limitation, Tuj1, S100β, galactocerebroside and/or MBP (myelin basic protein). For instance, as shown in the present Examples, the growth factor FGF2 maintains hESCs in an undifferentiated state, as evidenced by the high expression of SSEA-4 and OCT4 and low expression of the differentiation markers Brachyury and SOX17. Markers such as SSEA-4, OCT4, Brachyury and Sox17, as well as other markers indicative of differentiated and undifferentiated states, are known and routinely used in the art. Maintaining the undifferentiated state is critical for both deriving and maintaining stem cells.

Other undifferentiated cells encompassed by the present invention will also express similar and/or different markers characteristic of the undifferentiated state and/or of a differentiated state of the cell. Such markers are known or may be readily determined by the skilled artisan, and the expression of such markers may be analyzed to determine whether the cell is maintained in an undifferentiated state.

As used herein, the term "in the presence of a sustained release composition" with respect to a cultured cell, means that the cell is able to be contacted by sustained concentrations of the growth factor or other agent provided by the sustained release composition or other method of maintaining stable growth factor concentration over time. The cell and the sustained release composition may or may not be contained in the same well or other culture container. A cell is in the presence of a sustained release composition including, e.g., if the sustained release composition and the cell are separated from each other by a transwell or other divider, so long as fluid (e.g., culture media) and/or growth factors can be exchanged readily between the separated areas containing the cell and the sustained release composition.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, N.Y.: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 4 28-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nuc. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218. The skilled person will know and be able to use these and other techniques routine in the art to practice the present invention.

II. Overview

As discussed supra, present methods for culturing undifferentiated cells, such as stem and/or progenitor cells, are faced with at least two substantial difficulties. First, growth factors, such as FGF2, must be added frequently to the cultures, thereby making the culture of such cells a time consuming, laborious and expensive undertaking Standard protocols that add growth factor daily for ESC and every three days for NSC result in significant variations of growth factor concentrations to which the cells are exposed. Second, in the case of culturing undifferentiated cells such as stem cells and/or progenitor cells, a significant amount of unwanted, spontaneous differentiation of the cells occurs during culturing, even when growth factors such as FGF2 are administered daily to inhibit such differentiation. Hence, not only does the invention substantially reduce the labor and effort required to culture and maintain undifferentiated cells in an undifferentiated state, the resulting cultures exhibit surprisingly less spontaneous differentiation (resulting in less heterogeneity in the culture), and are therefore of unexpectedly improved quality, and therefore, utility, compared to cells cultured by currently available methods.

As an instance, and not by way of limitation, the Examples provided herein describe experiments where hESCs, iPSCS, RPESCs and NSCs were cultured using a sustained release composition containing a stable form of the growth factor FGF2 that provided a stable concentration range of FGF2 protein for up to 7 days or more (e.g., up to 35 days), by minimizing variation of growth factor concentration (e.g., as shown in Example 2, FGF2 concentration in the cell cultures was maintained in the range of 80-100% over 3 days in cultures containing FGF2-containing microspheres), significantly improving the stability of undifferentiated hESCs, iPSCS, RPESCs, NSCs and NPCs. In one Example, hESCs cultured in the presence of a sustained release composition containing FGF2 were maintained in an undifferentiated state in the absence of MEFs or MEF conditioned media. Furthermore, sustained release of FGF2 greatly improved the pluripotency of a cell culture that had undergone differentiation (as shown in Example 6).

Thus, in certain aspects, the present invention provides novel methods for maintaining sustained, stable concentration ranges of one or more growth factors in biologically active form over an extended period of time, preferably over a period of one or several days, and more preferably for at least a week to maintain the cells in a more undifferentiated state than standard methods of cell culture can achieve.

It was also demonstrated in the present Examples that frequent manual administration of growth factor directly to NSC cultures (every 8 hours), rather than the standard protocol (every third day), also improved the stability of the undifferentiated NSC culture (i.e., more cells were maintained in the undifferentiated state, as measured by the expression of Nestin and Tuj1). Further, the absolute number of cells produced was significantly increased. Thus, in certain embodiments, the present invention provides improved methods for culturing cells, such as NSCs, by exposing the cells to a steady level of growth factors (i.e., stable concentration range) to maintain the cells in an undifferentiated state and produced increased numbers of cells.

Although the invention is not limited by any particular theory or mechanism of action, it is believed that the present culture methods ensure a stable concentration range of growth factor over time (e.g., at least one day, at least 2 days, at least 3 days, at least 4 days, at least 5 days, at least 6 days, at least 7 days, or longer) that more closely mimics the in vivo environment. Hence, in preferred embodiments, one or more growth factors may be delivered in sustained release formulations to a cell culture at the beginning of the culturing process, and no further media changes are required during the extended time period (e.g., for multiple days, and preferably for at least seven days). In another embodiment, the growth factor, such as FGF2, may be administered frequently to the cell culture, e.g., three or more times per day or continuously, every day of the culture. The end result is a more homogeneous, undifferentiated cell culture (i.e., a more stable undifferentiated cell population) containing significantly more cells.

In a preferred embodiment, the undifferentiated cell is a stem cell or progenitor cell; however, a person of skill in the art will appreciate that the present methods are useful for culturing any undifferentiated cell that requires frequent administration of a growth factor or other agent.

III. Stem and Progenitor Cells

In certain embodiments, the present methods are useful for maintaining ESCs, in an undifferentiated state in standard culture dish surfaces. In another aspect of the invention, the present methods are useful for rescuing an ESC culture from differentiation restoring differentiated ESCs back to an undifferentiated state by culturing the ESCs in the presence of a sustained stable concentration range of growth factor, preferably FGF2. The present methods are useful for culturing any mammalian ESCs, such as but not limited to human, rat, pig, sheep, mouse, or non-human primate ESCs. ESCs can be derived according to any suitable method known in the art [Thomson et al., 1998; Amit, 2000 and Cowan et al., 2004; see also, U.S. Pat. Nos. 5,843,780; 6,200,806; and 7,029,913 (all by Thomson)], or by modifications of those protocols to include sustained levels of growth factor(s), as described herein.

Human ESCs (hESCs) are characterized for example by high expression of Octamer-binding protein 4 (Oct-4) (GenBank® Accession No. NM_001159542.1 (mRNA), Swiss-Prot Reference No. Q01860.1 (protein)); Nanog (GenBank® Accession Nos. NM_024865.2 (mRNA), AAP49529.1 (protein)); SRY (sex determining region Y)-box 2 (Sox2) (GenBank® Accession Nos. NM_003106.3 (mRNA), NP_003097.1 (protein)), TRA-18-1, SSEA-4, and SSEA-3 (see, Henderson, J K et al. (2002); Stem Cells; 20(4):329-37 for description of expression of TRA-1-81, SSEA-4 and SSEA-3 markers in human ESCs), and low expression of markers of hESC differentiation, such as Brachyury (GenBank® Accession Nos. NM_080646.1 (mRNA, variant A), NM_080647.1 (mRNA, variant C), NM_005992.1 (mRNA, variant B), AAB94018.1 (protein)), SRY (sex determining region Y)-box 17 (Sox17) (GenBank® Accession Nos. NM_022454.3 (mRNA), NP_071899.1 (protein)), Forkhead box A2 (Foxa2) (GenBank® Accession Nos. NM_021784.4 (mRNA, variant 1), NM_153675.2 (mRNA, variant 2), and AAH06545.2 (protein)); paired box 6 (Pax6) (GenBank® Accession Nos. NM_000280.3 (mRNA, variant 1), NM_001604.4 (mRNA, variant 2), NM_001127612.1 (mRNA, variant 3), and ABB55263.1 (protein)); orthodenticle homeobox 2 (Otx2) (GenBank® Accession Nos. NM_021728.2 (mRNA, variant 1), NM_172337.1 (mRNA, variant 2); NP_068374.1 (protein, isoform a), NP_758840.1 (protein, isoform b); and SRY (sex determining region Y)-box 1 (Sox1) (GenBank® Accession Nos. NM_005986.2 (mRNA), NP_005977.2 (protein)). Appropriate markers of ESCs of various species of origin are known, and can be readily determined by one skilled in the art.

In one aspect of the invention, the present methods are also useful for maintaining neural stem and/or progenitor cells in an undifferentiated state in culture. In another aspect of the invention, the present methods are useful for rescuing a neural stem and/or progenitor cell culture from differentiation by culturing the cells in the presence of sustained concentration range of growth factor, preferably FGF2.

NSCs and NPCs which may be cultured according to the methods described herein can be identified by the expression of certain markers, such as one or more of Nestin (GenBank® Accession Nos. NM_006617.1 (mRNA), NP_006608.1 (protein)); fucosyltransferase 4 (alpha (1,3) fucosyltransferase, myeloid-specific) (FUT4) (LeX) (CD-15) (GenBank Accession Nos. NM_002033.3 (mRNA), NP_002024.1 (protein)); Musashi (GenBank Accession Nos. AB012851.1 (mRNA), BAA33962.1 (protein)); polycomb complex protein Bmi-1 (Bmi-1) (GenBank Accession No. NM_005180.8 (mRNA), NP_005171.4 (protein)); Sox1 (GenBank® Accession Nos. NM_005986.2 (mRNA), NP_005977.2 (protein)); SRY (sex determining region Y)-box 2 (Sox2) (GenBank® Accession Nos. NM_003106.3 (mRNA), NP_003097.1 (protein)); Hes1 (GenBank® Accession Nos. Y07572.1 (mRNA), CAA68857.1 (protein)); Hes5 (GenBank® Accession Nos. DQ272660.1 (mRNA), ABB83829.1 (protein)); fatty acid-binding protein, brain (BLBP) (GenBank® Accession Nos. NM_001446.3 (mRNA), NP_001437.1 (protein)); and CD133 (GenBank® Accession Nos. NM_006017.2 (mRNA, variant 1), NM_001145847.1 (mRNA, variant 2), NM_001145848.1 (mRNA, variant 3), NM_001145852.1 (mRNA, variant 4), NM_001145851.1 (mRNA, variant 5), NM_001145850.1 (mRNA, variant 6), NM_001145849.1 (mRNA, variant 7), NP_006008.1 (protein, isoform 1), NP_001139320.1 (protein, isoform 2), NP_001139324.1 (protein, isoform 4), NP_001139323.1 (protein, isoform 5), NP_001139322.1 (protein, isoform 6), and NP_001139321.1 (protein, isoform 7), and no or relatively low levels (compared to a differentiated cell) of markers including without limitation, Tuj1, S100β (GenBank® Accession Nos., e.g., NM_006272.2 (mRNA), NP_006263 (protein) (other isoforms are also described and available from GenBank®)), galactocerebroside (GenBank® Accession Nos. NM_000153.3 (mRNA), NP_000144.2 (protein)) and/or MBP (myelin basic protein) (GenBank® Accession Nos., e.g., NM_001025081.1 (mRNA), and NP_001020252 (protein) (other isoforms are also described and available from GenBank®)).

As used herein, "neural" means the nervous system and includes glial cells and neurons. NPCs can also express high levels of helix-loop-helix transcription factors NeuroD, Atoh1, and neurogenin1 and neurogenin2 NSC cultures typically contain a mixture of NSCs and NPCs, and both may be cultured according to the methods of the present invention. [See, Abramova et al, Developmental Biology 2005 283:269-81; Beckervordersandforth, Cell Stem Cell (2010) 7:744-758; Shoemaker et al.; Plos One (2010) 5:e9121.]

NSCs and NPCs have the potential to differentiate into neural cells, such as, e.g., neurons, glia, astrocytes, retinal neurons, photoreceptors, oligodendrocytes, olfactory cells, hair cells, supporting cells, and the like.

In certain aspects, the present invention provides methods that are useful for culturing undifferentiated cells, such as ESCs, NSCs and NPCs, as well as related cell types. For example, the blastocyst contains parts that yield stem cells known as epiblast stem cells, and the nervous system contains several subtypes of NSCs. The advantage of the sustained release methods over daily or every 3 day administration methods of the present invention for these subtypes is expected to be the same as for ESCs, NSCs and NPCs. In other aspects, the present invention provides methods for culturing other undifferentiated cells, such as e.g., immature neural cells, wherein the cell is maintained in the undifferentiated state. In some aspects, in addition to ESCs, NSCs and NPCs, as well as iPSCs, MSCs and CSCs undifferentiated cells can include, without limitation, stem and/or progenitor cells of the skin, hair, gut, and blood, as well as other stem and/or progenitor cells including adipose, renal, epiblast, and bone marrow stem and/or progenitor cells, among many others.

In other aspects, the present invention provides methods that are useful for culturing undifferentiated cells, such as iPSCs, RPESCs, HSCs, MSCs, and CSCs. RPESCs can be expanded many fold in vitro and produce a wide variety of progeny from diverse developmental lineages (including mesoderm and ectoderm). RPESCs are capable of producing retinal cells, and they also are capable of producing a much wider repertoire of progeny, including bone, muscle and adipocytes. These cells and how to identify and/or isolate them are described in detail in U.S. Patent Application Publication No. 2009/0274667 by Temple et al. Such cells can also be cultured according to the methods of the present invention.

iPSCs are useful for both in vitro study of stem cells (e.g., factors controlling stem cell differentiation) and for the application of iPSCs for the treatment of disease. iPSCs can be derived from murine and human fibroblasts by introducing four specific transcription factors, SOX2 (GenBank® Accession Nos. NM_003106.3 (mRNA), NP_003097.1 (protein)), OCT4 (GenBank® Accession No. NM_001159542.1 (mRNA), Swiss-Prot Reference No. Q01860.1 (protein)), Kruppel-like factor 4 (gut) (KLF4) (GenBank® Accession Nos. NM_004235.4 (mRNA) and NP_004226.3 (protein)), and myc proto-oncogene protein ("c-MYC") (GenBank® Accession Nos. NM_002467.4 (mRNA) and NP_002458.2 (protein)), into the fibroblasts by viral transduction. [See, Lowry, W. E., et al. (2008). Proc. Natl. Acad. Sci. USA 105, 2883-2888; Maherali, N., et al. (2007). Cell Stem Cell; 1, 55-70; Park, et al. (2008). Nature 451, 141-146; Takahashi, K., and Yamanaka, S. (2006). Cell; 126, 663-676; Takahashi, K. et al. (2007). Cell 131, 861-872; and Yu, J. et al. (2007). Science; 318, 1917-1920; Stadtfeld and Hochedlinger (2010) Genes Dev; 24:2239-2263; Hochedliner and Plath (2009) 136; 509-523.] It has also been reported that OCT4, SOX2, NANOG, and LIN-28 (GenBank® Accession Nos. NM_024674.4 (mRNA), and NP_078950.1 (protein)) are sufficient to reprogram human somatic cells into pluripotent stem cells. Importantly, FGF2 is also used in the process of reprogramming fibroblast to the pluripotent state (i.e., for deriving iPSCs from fibroblasts). Furthermore, in culture, iPSCs are dependent on FGF2 in order to be maintained in an undifferentiated state. [See, Takahashi et al. Cell, Volume 131, Issue 5, 861-872, 30 Nov. 2007.]

MSCs can be obtained from a variety of tissues from the embryo through adulthood. For example, they can be extracted from the umbilical cord tissue, namely Wharton's jelly and umbilical cord blood or from amniotic fluid. MSCs can also be obtained from the developing tooth bud of the mandibular third molar, from the bone marrow, skeletal muscle, poeriosteium, lung, dermis and from adipose tissue. MSCs are widely present in the adult and can be extracted from a great variety of tissues. [See, Lu et al, Haematologica, 2006 91: 1017-26; Zeddou et al, Cell Biol Int 2010. vol 34:693-701; Lee et al Cell Physiol Biochem 2004 14:311-324; Rosenbaum et al 2008; Organogenesis 4:23027.] Rosenbaum et al. describes surface markers that can be used to identify MSCs.

Cancer stem cells (CSCs) are tumorigenic and may generate tumors through the stem cell processes of self-renewal and differentiation into multiple cell types. CSCs are thought to persist in tumors as a distinct population that can cause relapse and metastasis by giving rise to new tumors. Development of specific therapies targeted at CSCs are needed, e.g., for the treatment of cancer. Thus, it is useful to culture these cells in order to study them and to develop such therapies. However, CSCs are often very difficult to culture from primary tumor samples, illustrating their dependence on the growth factor environment found in vivo. Thus, improved methods for their culture are needed. CSCs can be cultured according to the present invention in the presence of a sustained concentration range of growth factor, in order to maintain them in an undifferentiated state. Primary tumors from a variety of sources are frequently FGF2 dependent and, in some cases, show superior growth in FGF2 [see, Lee et al, Cancer Cell (2006), vol 9 391-403; Ricci-Vitiani et al; Nature; 445 pp 111-115; New Yeoman, J Cell OPhysiol (1992) 150:320-326].

Hematopoietic stem cells (HSCs) can be isolated from bone marrow or peripheral blood. Methods for isolation of HSCs are described, e.g., in Hawley et al; Methods Enzymol; 2006; 419:149-179; and Challen et al, Cytometry A; 2009; 75; 14-24. HSCs are very difficult to culture ex vivo. However, FGF2 can help preserve their self-renewal [see, Yeoh et al, Stem Cells; 2006, 24:1564-1572.]

Non-limiting examples of stem cells and related progenitor cells that may be cultured according to the methods of the invention include, e.g., skin stem cells, spermatagonial stem cells, hair follicle stem cells, cancer stem cells, bone marrow stem cells, gut stem cells, hematopoietic stem cells, adipose stem cells, mouse embryonic stem cells, human embryonic stem cells, retinal pigment epithelial stem cells, mesenchymal stem cells, epiblast stem cells, renal stem cells, amniotic stem cells, umbilical blood stem cells, endothelial stem cells, and neural crest stem cells. Progenitor cells related to the above stem cells (i.e. derived from such stem cells) may also be cultured according to the present invention. All stem cells requiring growth factor to maintain the undifferentiated state. Any stem or progenitor stem cells now known or to be discovered may also be cultured according to the methods of the present invention. Stem and progenitor cells may be derived by the skilled artisan, and such methods are known in the art. Many stem cells are also commercially available or available from cell banks, such as, e.g., the WiCell Reseach Institute, National Stem Cell Bank, Madison, Wis.

IV. Cell Culture Methods

The present invention provides novel and improved methods for culturing undifferentiated cells, such as but not limited to stem and/or progenitor cells. For culturing stem and/or progenitor cells, appropriate culture medium is known and described in the art. [See, e.g., Amit et al., 2000, supra; Fasano et al., 2010, supra; Ludwig et al., 2006, supra; Bendall, et al., 2007, supra; Qian et al., 1997, supra, Fasano et al., 2007, supra; and Shen Q, et al. (2004) Science 304, 1338-40.] For example, cells can be cultured in serum free DMEM/high-glucose supplemented with N2 and B27 solutions and growth factors. Typically cells are incubated at 37° C., and 5% $CO_2$ in tissue culture treated wells. Optionally, cells can be cultured in the presence of feeder cells, such as mouse embryonic fibroblasts (MEFs); however, as demonstrated by the present Examples, the present invention provides sustained release compositions that eliminate the need for feeder cells. Such methods are well known in the art. [See, e.g., Amit et al., 2000; Fasano et al, 2010; Ludwig et al., 2006; Bendall, et al., 2007; Qian et al., 1997, Fasano et al., 2007; and Shen et al., 2004.] Specific culture conditions are readily determined and adjusted by the ordinarily skilled artisan.

Typically, ESCs are grown until density is deemed suitable for the appropriate experiments being carried out by the investigator (typically one week). At this point, ESCs are passaged either as single cells or cell aggregates onto MEF feeders, or tissue culture treated plastic dishes coated with an extracellular matrix (Fasano et al., 2010). Typically, NSCs and/or NPCs are grown until density is deemed suitable for the appropriate experiments being carried out by the investigator (typically one week). At this point, NSCs and/or NPCs are passaged as either single, dissociated cells or cell aggregates onto tissue culture treated plastic dishes coated with an extracellular matrix or non-tissue culture treated plates with no extracellular matrix when floating NSC (neurosphere) cultures are needed (Fasano et al., 2007).

Standard culture methods for the culture of stem cells such as, but not limited to, iPSCs, MSCs, CSCs and SCSCs are known in the art. For example, methods for the culture of iPSCs are described in detail, e.g., in Maherali and Hochedlinger, Cell Stem Cell 2008 3:595-605. Methods for the culture of MSCs are described in Sotiropoulou P A, et al.; Stem Cells. 2006 February; 24(2):462-71. Methods for the culture of CSCs are described, e.g., in Cao, L. et al. BMC Gastroenterol. 2011 Jun. 14; 11(1):71; and Wakimoto et al. Cancer Res. 2009 Apr. 15; 69(8):3472-81. Methods for the culture of SCSCs are described, e.g., in Lowry et al. Exp Neurol. 2008 February; 209(2):510-22; Yan J. et al., PLoS Med. 2007 February; 4(2):e39; and Yeoh et al, stem cells 2006, 24:1564-1572.

In the present methods, the undifferentiated cells are incubated in the presence of sustained concentration range of growth factor. In certain embodiments, the undifferentiated cells are incubated in the presence of a sustained release composition, such as, e.g., PLGA microspheres. In some aspects, the undifferentiated cells can be incubated with two or more sustained release compositions that are the same or different compositions containing the same or different growth factor(s). In certain aspects, the cells are cultured in the constant presence of one or more growth factors by frequent feeding with the growth factor (e.g., continuously, or every 2, 4, 6, or 8 hours). Preferably cells are fed more than every 8 hours with the desired growth factors. According to the present methods, the stable concentration range of growth factors are useful for maintaining cells, such as stem or progenitor cells, in an undifferentiated state and are also effective for increasing the number, homogeneity and quality of progeny produced.

For "frequent feeding" of growth factors to a cell culture (e.g., growth factor added to culture every few hours or continuously), the growth factor may be administered to the cell culture by any suitable method, such as e.g., by pipette or dropper, or may be dripped in by an automatic cell feeding system (i.e., mechanically).

V. Sustained Release Compositions

The invention provides sustained release compositions that maintain sustained concentrations, or concentration range, of growth factors in the cell culture media over an extended period of time (e.g., over a period of several days and, preferably, for at least seven days). It is to be understood that the present invention is not to be limited to any one particular or even to several sustained release compositions, such as those described herein. The methods of the present invention may be practiced using any suitable sustained release composition or preparation (e.g., tissue culture plate coating), so long as the growth factor(s) provided by the sustained release composition or preparation is provided in a manner that results in sustained, stable concentration ranges of growth factor, as described herein.

In other embodiments, growth factors may be added directly to a cell culture, e.g., multiple times per day, or continuously. In a specific embodiment, FGF2 is administered three times per day, every 8 hours, directly to an NSC culture causing unexpected and significant improvement in the differentiation state and number of cells compared to standard methods of culture (feeding FGF2 to the cells every 3 days).

Non-limiting examples of sustained release compositions that may be used in the methods of the invention include, e.g., microspheres (e.g., poly(DL-lactide-co-glycolide) (PLGA) microspheres), anhydrous poly-vinyl alcohol (PVA), millicylinders, alginate gels, biodegradable hydrogels, liposomes, complexing agents, continuous micropumps, nanoparticles and any biocompatible material that releases growth factor over sustained periods. [See, e.g., Ashton, et al. (2007) Biomaterials, 28, 36, 5518; Drury, J. L. et al. (2003) Biomaterials; 24:4337-4351; U.S. Pat. No. 7,226,617 to Ding et al.; Simmons, C. A. et al. (2004) Bone; 35:562-569; Zhu, G. et al. (2000) Nat Biotech; 18:52-57, Biodegradable Hydrogels for Drug Delivery, K. Park et al, 1993, Technomic Publishing, Trans Am Ophthalmol Soc, K. Derwent et al, 2008; 106:206-13; see also published U.S. Patent Application Publication No. 2010/0021422.] In the present Examples, microspheres were prepared according to methods described in Zhu, G. et al. (2000) Nat Biotech; 18:52-57, modified using a standard double emulsion technique.

In some aspects, microspheres or microparticles of the present invention may comprise a combination of PLGA and PVA. [See, Edlund et al., Advances in Polymer Science Vol. 157, 2002, 67) lists on page 77 a number of different degradable polymers investigated for controlled drug delivery applications (e.g., polyglycolide, polylactide, etc.).] Thus, suitable sustained release compositions useful in the present invention could be made using these or other degradable polymers. PVA is one of a range of possible substances that can be used to stabilize microspheres produced by emulsion solvent evaporation techniques. PVA is used as a stabilizing/emulsifying agent. Varying the concentration of PVA can enable the size of the microspheres to be varied, which in turn can influence the release profile [see, e.g., Zhao et al. (2007) BioMagnetic Research and Technology; 5:2].

PLGA microspheres of the present invention can range in size from 10-40 μm, with an average diameter of 20 μm. The size can be controlled by varying the speed of the homogenizer, etc. In certain embodiments, larger particles can be used; varying the size of the microspheres can be guided by culture condition considerations, the desired kinetics of release, loading efficiency and amount of growth factor release.

In some embodiments, PLGA millicylinders may be used as a sustained release composition of the invention for the time release of growth factor(s) to cells in culture. As used herein, "millicylinders" are single cylindrical implants approximately 0.8-1.5 mm in diameter. [See, Zhu, G. et al. (2000) Nat Biotech; 18:52-57.] Yet another aspect of the invention includes the use of nanoparticles for the time release of growth factor(s) to cells, such as undifferentiated cells, in culture. As used herein, "nanoparticles" are defined as small particles that are typically sized in the range of 1-100 nanometers (nm), but also include sub-micron as well as larger particles encompassing the range of 1-1000 nm. [See, for example, Ya-Ping Li, et al., J. of Controlled Release, 71, 2001, pages 203-211; Mu, L. and Feng, S.; J. of Controlled Release; 86, 2003, 33-48; and Govender et al., J. of Controlled Release; 57, 1999, pages 171-185.]

Another aspect of the invention includes the suspension of microspheres in a hydrogel, which is considered biocompatible, biodegradable, and is compatible with cells in cell culture, such as stem and/or progenitor cells. The hydrogel matrix has multiple uses including but not limited to stabilizing in vivo applications of undifferentiated cells (e.g., stem and/or progenitor cells), generating three-dimensional cell cultures, and delivering drugs, growth factors and other agents into cell culture. The bioactive factor is released from the microsphere present in the hydrogel. Therefore, its rate of release can be adjusted in the same way as when there is no hydrogel (e.g., by changing the composition/molecular weight of polymers used to make the microsphere, changing protein loading in the microsphere, microsphere size, etc.). It was shown in Ashton et al. (supra), that the incorporation of microspheres containing alginate lyase into the hydrogel enable controlled release of this enzyme which in turn provides control over the rate of degradation of the hydrogel. [See, Ashton et al. (2007) (supra); Piantino et al., 2006, Exp Neurol., 201(2):359-67; see also, U.S. Pat. No. 7,226,617 to Ding et al.]

Another example of a sustained release composition of the invention includes an amorphous carbohydrate glass matrix, as described in detail in PCT publication number WO 93/10758, in which a bioactive agent such as FGF2 is incorporated into the carbohydrate glass matrix and controlled release or degradation is adjusted by addition of a hydrophobic substance. The present invention also provides coating plastic or glass culture dishes with a matrix that releases growth factor in a sustained manner. For example, the tissue culture plate time releases FGF2 and/or other growth factors coated or contained in the surface of the tissue culture plate or other container, over at least about 3, 4, 5, 6, or 7 days.

Typical concentrations of a sustained release composition (e.g., PLGA microspheres) for cell culture range from about 1 to about 300 ng/ml, preferably from about 1 to about 200 ng/ml, more preferably from about 1 to about 100 ng/ml, even more preferably from about 1 to about 50 ng/ml, and most preferably from about 1 to about 10 ng/ml or from about 1 to about 5 ng/ml. Typically, although not necessarily, about 7 μl per 1 ml of culture media of PLGA microsphere preparation (concentration 1000 microspheres per μl of preparation) are added to the culture.

The present invention contemplates the use of any growth factor in the sustained release compositions of the invention that is useful for maintaining cells in an undifferentiated state. Further, a sustained release composition of the invention may comprise two or more growth factors.

A preferred growth factor that may be used in the present invention is FGF2. However, other non-limiting examples of suitable growth factors or other cytokines include, e.g., epidermal growth factor (EGF), platelet-derived growth factor (PDGF), sonic hedgehog (Shh), leukemia inhibitory factor (LIF) and Wnt proteins (e.g., Wnt1 or Wnt3) or any growth factor that maintains the stem cell in an undifferentiated state. For example, spinal cord stem cells (SCSCs) are expanded by Shh [see, Lowry, N. et al. Exp Neurol. 2008 February; 209 (2):510-22]. Thus, in one embodiment, SCSCs are cultured in the presence of a stable concentration range of Shh in order to maintain the SCSCs in an undifferentiated state. In one embodiment, the SCSCs are cultured in the presence of a sustained release composition, e.g., PLGA microspheres or other composition, such as but not limited to those described herein, wherein the sustained release composition comprises Shh. Additionally, the sustained release composition can comprise one or more of $Mg(OH)_2$, heparin, dextran sulfate, and EDTA.

Concentrations of growth factors in the sustained release compositions of the invention can range from about 5% (w/v) to about 0.001%, from about 3% to about 0.05%, from about 2% to about 0.01%, and from about 1.0% to about 0.1%. In a specific embodiment, a sustained release composition comprises about 0.5% (w/v) FGF2. However, more or less FGF2 can be used depending on the specific culture conditions.

Sustained release compositions of the invention may further comprise agents that stabilize and/or complex with one or more growth factors contained in the composition. For example, the composition may further comprise heparin, which has been shown to stabilize FGF2. [See, Caldwell, M. et al. (2004); Exp Neurol; 188:405-420.] Another agent that can be included in the composition in place of or in addition to heparin is dextran sulfate. Concentrations of heparin and/or dextran sulfate can range from about 5% (w/v) to about 0.001%, from about 3% to about 0.05%, from about 2% to about 0.01%, and from about 1.0% to about 0.5%. In a specific embodiment, a sustained release composition comprises about 1.0% (w/v) heparin and/or dextran sulfate. However, more or less heparin or dextran sulfate can be used depending on the specific culture conditions. In addition, other polyanionic molecules that complex with FGF2 may be part of the present invention [J. Med. Chem., 2000, 43 (13), pp 2591-2600]. Covalent modifications of the growth factor that result in reduced degradation are also included. All modifications that result in sustained concentrations of growth factor in the stem cell growth media are expected to produce the same unexpected and surprising result of improved proliferation, more homogenous undifferentiated population of stem cells, and less stem cell differentiation.

Sustained release compositions of the invention may further comprise agents that modify the pH of the sustained release composition. For example, in a specific embodiment, $Mg(OH)_2$ is added to the composition to neutralize an acidic environment, e.g., of a PLGA microsphere. Concentrations of $Mg(OH)_2$ can range from about 15% (w/v) to about 0.05%, from about 10% to about 0.1%, and from about 5% to about 1.0%. In a specific embodiment, a sustained release composition comprises about 3.0% (w/v) $Mg(OH)_2$. However, more or less $Mg(OH)_2$ can be used depending on the specific culture conditions. The compositions of the invention may also optionally comprise agents such as e.g., EDTA, gum arabic, sucrose, $MgCO_3$, and BSA.

In a specific embodiment of the invention, a sustained release composition is a PLGA microsphere, having a diameter of about 10-50 microns, comprising 0.5% FGF2, 3% $Mg(OH)_2$, 1.0% heparin, and 1 mM EDTA. In another embodiment, a sustained release composition is a PLGA microsphere, having a diameter of about 10-50 microns, comprising 0.5% FGF2, 3% $Mg(OH)_2$, 1.0% dextran sulfate, and 1 mM EDTA. In either embodiment, the sustained release composition releases FGF2 over a period of at least about 1, 2, 3, 4, 5, 6, or 7 days, or longer, e.g., 2 weeks, 3 weeks, 4 weeks, 5 weeks, or longer. Preferably, the composition releases FGF2 over at least 3 days or longer.

The kinetics and quantities of release of a growth factor from a sustained release composition will depend on the specific composition and size of the sustained release composition, the loading efficiency, the unreleased reservoir, the degradation rate of the growth factor as well as the concentration of the growth factor and other agents contained in the composition. The release kinetics and amount of growth factor released, e.g., into the cell culture, are readily determined by the skilled artisan. Preferably, a sustained release composition releasing FGF2 will release about 10 ng/ml FGF2 per day over at least about 3 to 7, 4 to 7, or 5 to 7 days for native FGF2 although less is needed for stabilized forms of FGF2. For example, given 1 mg of FGF2 microspheres in 1 ml of PBS containing 0.2% Tween 20, 1% BSA, 10 ug/ml heparin, and 1 mM EDTA, and based on 0.2% release of protein, 10 ng/ml of FGF2 will be achieved in the culture medium per day over a period of at least about 3 days. The level of FGF2 and other growth factors needed to stabilize undifferentiated cells (i.e., maintain them in an undifferentiated state) may depend on the release kinetics and degradation kinetics; however, preferably, the concentration of FGF2 in the culture is maintained in the range of from about 1 ng/ml to about 10 ng/ml or higher, e.g., 15 ng/ml or 20 ng/ml, or higher, over about 1 day, 2 days, 3 days, 4 days, 5 days, 6 days 7 days, or longer, e.g., 2 weeks, 3 weeks, 4 weeks, 5 weeks, or longer.

V. Assaying Cell Differentiation

A variety of methods can be utilized to determine whether an undifferentiated cell has been maintained as an undifferentiated cell. For example, cells in hESC cultures can be examined for the expression of markers of undifferentiated cells, such as, but not limited to, OCT4, NANOG TRA-1-81, SSEA-4, and/or SSEA3. NSCs and NPCs can be examined for expression of one or more markers such as, but not limited to, Nestin, Lex (CD-15), Sox-1, Sox-2, CD133, Musashi, Bmi-1, Hes1 and/or Hes5.

Such cells may also be examined for expression of markers of differentiating or differentiated cells, such as, but not limited to, Brachyury, Sox17, Foxa2, Otx2, Sox1 and/or SSEA-1 (for hESCs); and such as Tuj1, S100β, O4, and myelin basic protein (MBP) (for NSCs and NPCs). Gene and/or protein expression of such markers can be determined, e.g., by quantitative PCR, FACS analysis, and/or ELISA. Such methods are well known in the art. Such markers are also useful for characterizing differentiating cells of other non-human species of origin, and appropriate markers are known and readily determined by the ordinary skilled artisan.

It is to be understood that the methods of the present invention can be used for culturing many types of undifferentiated cells, such as but not limited to stem cells, progenitor cells, neural cells such as immature neural cells, etc., from any species of origin. A person of skill in the art can readily determine which markers are appropriate for characterizing the specific cell being cultured.

For stem cells, specifically, assessment of stem cell differentiation (or maintenance of stem cells in an undifferentiated state) also can be determined by analysis of morphological features of the stem cell culture. hESCs exhibit high nucleus to cytoplasm ratio with prominent nucleoli, and are rounded and typically grow in colonies that lie tightly packed together. The borders of these colonies are very tight, rigid and well-defined. NSCs exhibit a flat, in some cases pavemented morphology. NSCs tend to grow as clones, or in groups held very closely together, where they might take on a square or roughly triangular appearance (Temple, 1989; Thomson et al, 1998). Additionally, NSCs can be put in culture as floating aggregates known as neurospheres. After one week, these neurospheres are dissociated into single cells and replated in the same conditions. A properly maintained NSC line will continue to generate new spheres at the same rate or higher than the previous passage. A deficit in NSC maintenance would result in reduced neurosphere formation after passage (Fasano et al, 2007).

VI. Kits

The sustained release compositions for culturing undifferentiated cells, such as stem and/or progenitor cells, described herein can be provided in a kit. The kit can include one or more sustained release compositions of the invention (e.g., PLGA microspheres) containing one or more growth factors suitable for maintaining such cells in an undifferentiated state; and, optionally, (b) informational material. Each sustained release composition can be provided separately in the kit, if more than one composition is included, or they can be provided as one or more mixtures of different sustained release compositions. In addition to the active compound (e.g., growth factor), the sustained release composition of the kit can include other ingredients, such as a solvent or buffer, a stabilizer, a preservative, and/or an additional agent (e.g., growth factor) for culturing and maintaining cells in an undifferentiated state, as described herein. The sustained release composition can be provided in the kit as ready-to-use, i.e., containing all agents, e.g., pH stabilizing agents (e.g., $Mg(OH)_2$), growth factor stabilizers (e.g., heparin), and the active agent, e.g., growth factor(s), to be included in the composition upon addition to a cell culture. Alternatively, the kit can provide some or each of the components of the final sustained release composition separately, with instructions for how to combine the components prior to use.

The informational material can be descriptive, instructional, marketing or other material that relates to the methods described herein and/or to the use of the sustained release composition for the methods described herein. For example, the informational material relates to the use of the sustained release composition provided in the kit for the culture of undifferentiated cells (e.g., stem and/or progenitor cells). The kits can also include paraphernalia for administering one or more compounds to a cell (e.g., pipette, dropper, etc.).

The informational material of the kits is not limited in its form. In many cases, the informational material (e.g., instructions) is provided in printed matter, such as in a printed text, drawing, and/or photograph, such as a label or printed sheet. However, the informational material can also be provided in other formats, such as Braille, computer readable material, video recording, or audio recording. Of course, the informational material can also be provided in any combination of formats.

The kit can include one or more containers for the sustained release composition(s). In some embodiments, the kit contains separate containers, dividers or compartments for the composition and informational material. For example, the composition can be contained in a bottle, tube or vial, and the informational material can be contained in a plastic sleeve or packet. In other embodiments, the separate elements of the kit are contained within a single, undivided container. For example, the sustained release composition is contained in a bottle, tube or vial that has attached thereto the informational material in the form of a label.

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1

FGF2 Fluctuation in Standard hESC Culture Conditions

This Example demonstrates that FGF2 concentrations fluctuate dramatically in standard hESC culture conditions.

WA-09 hESCs (WiCell Research Institute, National Stem Cell Bank, Madison, Wis.) were plated on tissue culture treated dishes or plates in standard mouse embryonic fibroblast (MEF) feeder (Global Stem Inc. (Rockville, Md.)) or non-MEF (Matrigel) (BD Biosciences, Bedford, Mass.) conditions in complete medium containing 10 ng/ml FGF2 or in MEF-conditioned medium (MEF CM) containing 10 ng/ml FGF2. Complete culture medium contained DMEM/F12 (Invitrogen, Carlsbad, Calif.), containing L-Glutamine (Invitrogen), Minimal Essential Amino Acids (Invitrogen), 20% Knockout Serum Replacement (Invitrogen), and 2-Mercaptoethanol (Invitrogen), and MEF CM was the same complete culture medium, but prior to use had been allowed to bathe MEFs for 24 hours.

Figure 1B:
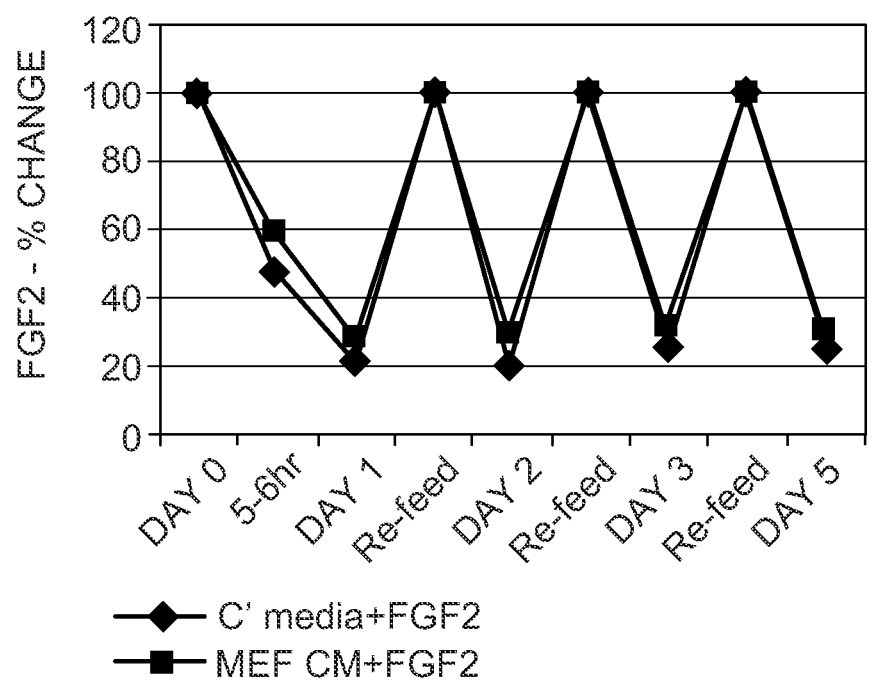

The media was changed daily according to standard hESC culture technique (see, Fasano et al., 2010). Before each re-feed (change of media), a sample of media was collected and the levels of FGF2 were quantified using a cytokine bead kit and FACS according to the manufacturer protocols (BD Cat#558327). After 5 hours of culture, in both MEF and Matrigel conditions, FGF2 levels were already reduced by greater than 50%, and by the time of the next media change (24 hours later), FGF2 levels were not detectable (FIG. 1A and FIG. 1B). These results demonstrated that the standard method for maintaining hESCs in culture is sub-optimal due to growth factor instability.

Example 2

FGF2-Containing Microspheres Sustain FGF2 Levels in hESC Cultures

WA-09 hESCs (WiCell Research Institute) were plated on Day −1 on standard MEF (Global Stem Inc.) on tissue culture treated culture dishes or plates in standard hESC media containing DMEM/F12 (Invitrogen, Carlsbad, Calif.), containing L-Glutamine (Invitrogen), Minimal Essential Amino Acids (Invitrogen), 20% Knockout Serum Replacement (Invitrogen), and 2-Mercaptoethanol (Invitrogen) and 10 ng/ml FGF2. Biodegradable PLGA microspheres were produced using 0.5% FGF2 (R&D® Systems), 3% $Mg(OH)_2$, 1:1 weight ratio of heparin to FGF2 and 1 mM EDTA ("FGF2-microspheres").

Figure 2:
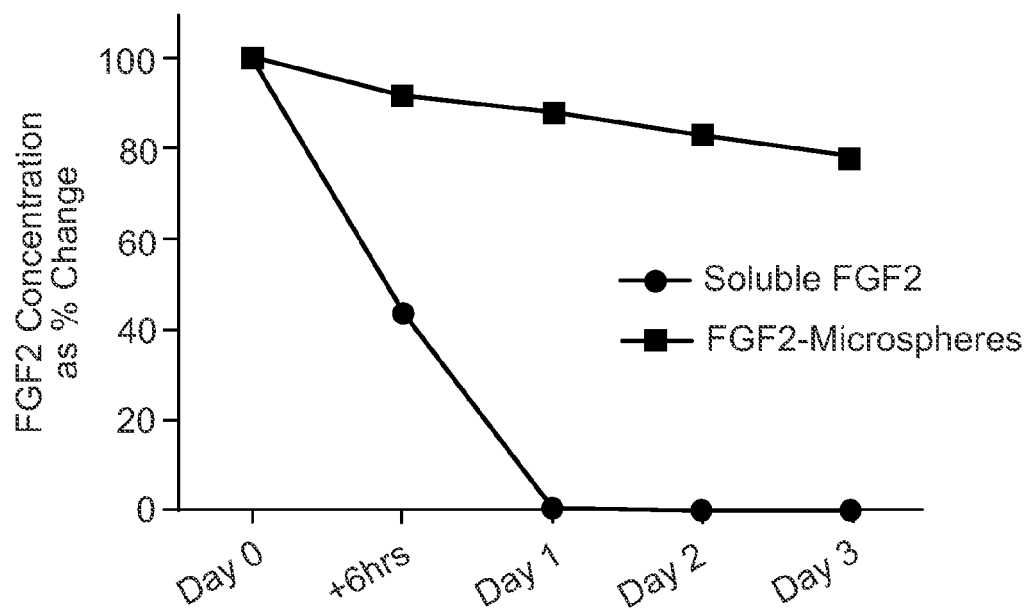
FIG. 2 is a graph showing the percent (%) change in FGF2 concentration after 6 hours, on Day 1, Day 2, and Day 3 in the culture media of cells cultured with or without FGF2-containing PLGA microspheres ("FGF2-microspheres") added on Day 0, following replacement of the culture media with fresh complete media containing 10 ng/ml FGF2. Percent (%) change is relative to the starting concentration of FGF2 on Day 0, immediately following replacement of the culture media and before addition of microspheres (in the FGF2-microspheres group).

To measure FGF2 concentration in the hESC cultures over time, on Day 0, the culture media in the plated hESCs was changed and replaced with fresh complete media containing 10 ng/ml FGF2. Immediately after the media was replaced, a sample was collected in order to determine the concentration of FGF2 on Day 0 (the starting concentration). Just after the media sample was collected, FGF2-containing microspheres were added to one group ("FGF2-microspheres"). 7 µl per 1 ml of culture media of FGF2-microsphere preparation (concentration 1000 microspheres per 1 µl of preparation) were used. Six (6) hours later, and then every 24 hours (calculated from the time of media replacement on Day 0), a sample of medium was collected and the level of FGF2 in each culture was quantified using a cytokine bead kit and FACS according to manufacturer protocols (BD Cat#558327). Consistent with Example 1, above, FGF2 levels in the soluble FGF2 cultures declined rapidly, and FGF2 could not be detected after 1 day of culture. However, in the FGF2-microsphere culture, FGF2 levels were stable, with only 20% of the starting level of FGF2 being reduced by Day 3 (FIG. 2). These data demonstrated that sustained release compositions, such as PLGA microspheres, can be used to maintain stable growth factor levels in cell culture, thereby offering a solution to a current problem with the standard methodology for stem cell culture; namely rapid FGF2 level fluctuation and decline.

Example 3

Culture of hESCs with FGF2-Containing PLGA Microspheres

On Day −1, WA-09 hESCs were plated on standard mouse embryonic fibroblast (MEF) and non-MEF conditions as described in Example 1, above, in complete culture media containing DMEM/F12 (Invitrogen, Carlsbad, Calif.), containing L-Glutamine (Invitrogen), Minimal Essential Amino Acids (Invitrogen), 20% Knockout Serum Replacement (Invitrogen), 2-Mercaptoethanol (Invitrogen) and 10 ng/ml FGF2. The cell culture media was not changed for the 5-day duration of the experiment.

Biodegradable PLGA microspheres containing 0.5% soluble human FGF2 (R&D Systems), 3% $Mg(OH)_2$, 1:1 weight ratio of heparin to FGF2 and 1 mM EDTA ("FGF2 microspheres") or control microspheres containing 3% $Mg(OH)_2$, 1:1 weight ratio of heparin to FGF2 and 1 mM EDTA, but not FGF2 ("empty microspheres"), were added to some of the cell cultures on Day 0 (24 hours after plating), following replacement of the culture media with complete hESC culture media supplemented with 10 ng/ml FGF2, either directly to the well containing hESCs or in a transwell above hESCs. 7 µl per 1 ml of culture media of FGF2-microsphere preparation (concentration 1000 microspheres per 1 µl of preparation) were used. In a control group, 10 ng/ml soluble human FGF2 was added to the culture daily ("soluble FGF2").

Figure 3:
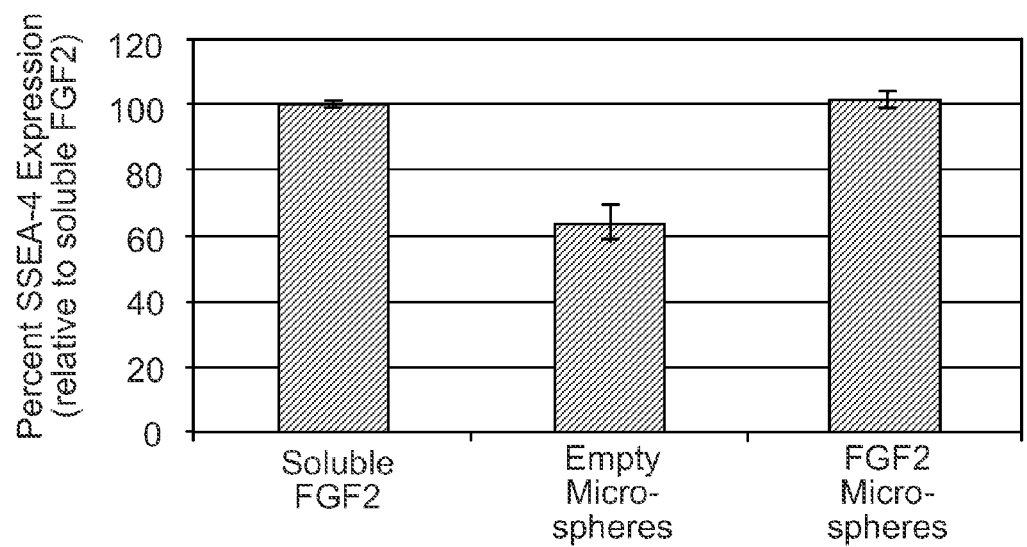
FIG. 3 is a graph showing the percent (%) (relative to soluble FGF2 treated group) of SSEA-4 mRNA expression in human ESCs treated with soluble FGF2, FGF2-containing PLGA microspheres ("FGF2-microspheres") or empty microspheres, 5 days after treatment.

After 5 days, cells were assessed for SSEA-4 expression via FACS. The SSEA-4-antibody used for FACS staining was obtained from BD Biosciences. As expected, cells cultured under the empty microsphere condition exhibited less SSEA-4 expression after five days compared to cells that received daily soluble FGF2 (FIG. 3). However, cells cultured with FGF2-microspheres exhibited a slight increase of SSEA-4, indicating that these cells underwent even less spontaneous differentiation than with daily soluble FGF2 treatment (FIG. 3). Further, undifferentiated morphology of the cells was observed in cells treated with soluble FGF2 or FGF2 microspheres, and differentiated morphology was observed in the negative control (empty microspheres).

Figure 4:
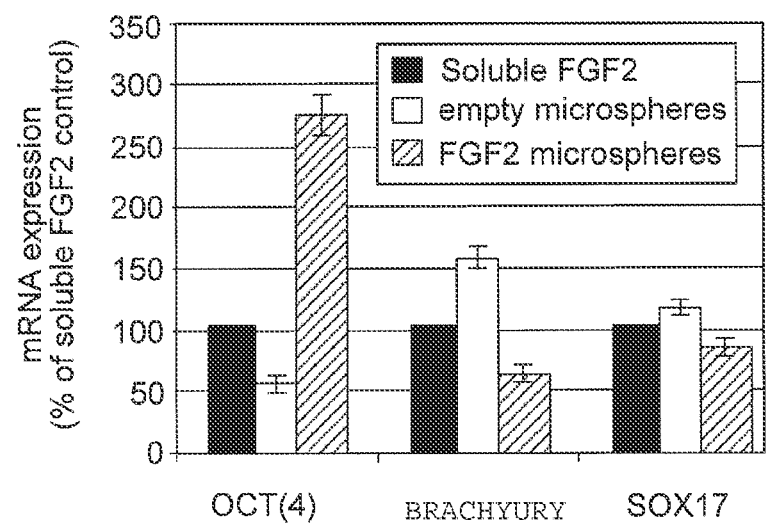
FIG. 4 is a graph showing the percent (relative to soluble FGF2 treated group) of OCT4, Brachyury and SOX17 mRNA expression in human ESCs treated with soluble FGF2, FGF2-containing PLGA microspheres or empty microspheres (negative control), 5 days after treatment.

In addition to FACS analysis, mRNA expression levels of OCT-4, an undifferentiated hESC maker, and the differentiation markers Brachyury and Sox17 were determined by quantitative RT-PCR. Verified TaqMan probes from Applied Biosystems™ (Foster City, Calif.) were used to assess gene expression. In culture, hESCs typically undergo low levels of spontaneous differentiation using standard stem cell culture methods (i.e., daily addition of soluble FGF2). Surprisingly, compared to daily soluble FGF2 treatment, hESCs cultured in the presence of the stable concentration range of FGF2 provided by the PLGA microspheres exhibited significantly less spontaneous differentiation, as indicated by decreased mRNA expression levels of Brachyury and Sox17 and higher OCT-4 mRNA expression levels (FIG. 4). Similar results were obtained when FGF2 microspheres were placed in transwells above hESCs, indicating that direct contact of the microspheres with the stem cells was not required. Results from the mRNA expression analysis of OCT-4, Brachyury and SOX17 were consistent with morphological culture homogeneity.

Thus, the culture methods used in this Example resulted in the maintenance of a stable FGF2 concentration range in the hESC cultures, and in the surprising decrease in spontaneous differentiation of hESCs, a problem associated with standard culture methods (i.e., daily, direct addition of soluble FGF2 to the culture media). The methods described in this Example therefore provide the benefit of increasing the utility of cultured hESCs and significantly reducing the labor required to grow them.

Example 4

Sustained Release of FGF2 in Long-Term hESC Cultures

Figure 5A:
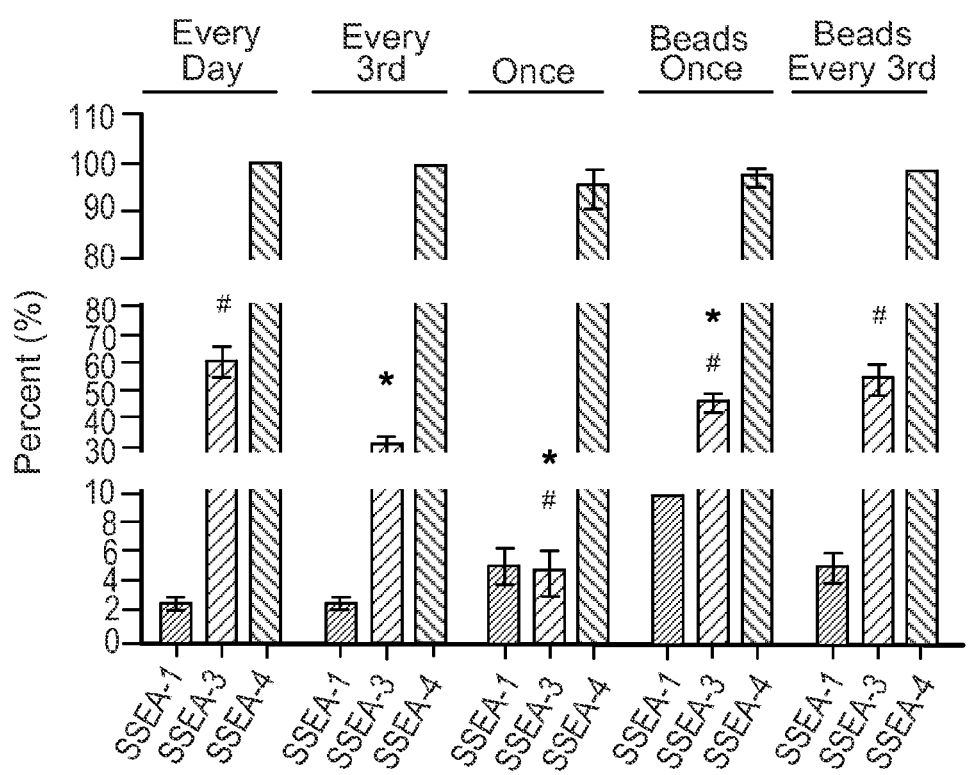
FIG. 5A is a graph showing the percent of cells that stained positive for SSEA-1, SSEA-3 and SSEA-4 protein on Day 35 in cultures of WA-09 hESCs that were fed every day, on Day 0 and then every third day for the duration of culture ("Every $3^{rd}$") or on Day 0 ("Once") with 10 ng/ml FGF2, or in cultures of WA-09 hESCs that were fed with FGF2-containing PLGA microspheres on Day 0 ("Beads Once") or on Day 0 and then every third day for the duration of culture ("Beads Every $3^{rd}$"). "*" indicates that p<0.05 compared to the "Every Day" group, for the same protein, and "#" indicates that p<0.05 compared to the "Every $3^{rd}$" group, for the same protein.

WA-09 hESCs were plated on standard MEF and cultured in complete hESC culture media containing 10 ng/ml FGF2, as described in Example 1, above. Biodegradable PLGA microspheres were produced using 0.5% FGF2 (R&D® Systems), 3% $Mg(OH)_2$, 1:1 weight ratio of heparin to FGF2 and 1 mM EDTA ("FGF2-microspheres"). 7 µl per 1 ml of culture media of FGF2-microsphere preparation (concentration 1000 microspheres per 1 µl of preparation) were used. Cells were either fed every day, every 3rd day, or once with 10 ng/ml soluble FGF2, or cells were fed every 3rd day with FGF2-microspheres or once with FGF2-microspheres. After 7 days, hESCs were passaged according to standard procedure [Fasano et al., 2010, supra], and some cells were analyzed by FACS to assess the expression of the pluripotency markers, SSEA-4 and SSEA-3, and the differentiation marker SSEA-1. Cells were passaged every 7 days, for 5 weeks. After 35 days, the percentage of cells that stained positive for SSEA-1, SSEA-3, and SSEA-4 in each group was determined. The expression data was similar for cells fed once with FGF2 microspheres or every $3^{rd}$ day. Cells that were fed FGF2-microspheres maintained high expression of pluripotency markers SSEA-3 and SSEA-4 and low expression of differentiation marker SSSEA-1, indicating that the cells were maintained in an undifferentiated state in the long-term culture (FIG. 5A).

Figure 5B:
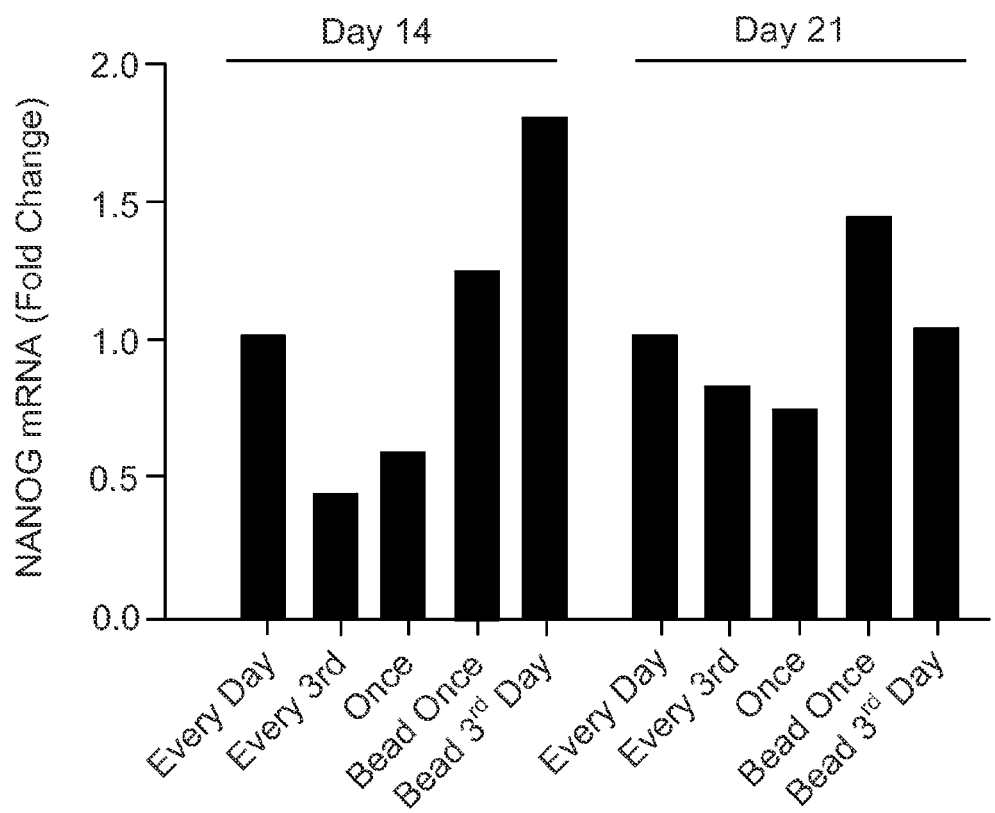
FIG. 5B is a graph showing fold change in mRNA expression of NANOG on Day 14 and Day 21 in WA-09 hESCs that were fed every day, on Day 0 and then every third day for the duration of culture ("Every $3^{rd}$") or on Day 0 ("Once") with 10 ng/ml FGF2, or in cultures of WA-09 hESCs that were fed with FGF2-containing PLGA microspheres on Day 0 ("Beads Once") or on Day 0 and then every third day for the duration of culture ("Beads $3^{rd}$ Day").

In addition to this, at Day 14 and Day 21, RNA was isolated from the cultured cells and mRNA expression of the pluripotency marker NANOG was quantified by qRT-PCR. Surprisingly, at both time points, there were higher levels of NANOG expression in all groups of cells cultured with FGF2 microspheres compared to cells fed every day with soluble FGF2. These results thus showed that cells cultured long-term in the presence of FGF2 microspheres had consistent pluripotent marker expression, and, in some assays, higher pluripotent marker expression levels than cells cultured using standard culture methods (FIG. 5B). The stable FGF2 levels provided by a sustained release composition, such as FGF2 microspheres, can therefore minimize the number of culture feeds and maintain hESCs in a more undifferentiated state.

Example 5

Sustained Range of FGF2 Concentration Maintains hESCs in a More Undifferentiated State without Feeder Cells or Feeder Conditioned Medium hESCs can be grown without MEF feeders only in the presence of MEF conditioned hESC media, or, in expensive, "special" media containing very high levels of FGF2. In this experiment, it was determined whether sustained FGF2 levels provided by FGF2 microspheres was sufficient for the culture of hESCs in the absence of MEF feeders, MEF conditioned hESC media, or special media. WA-09 hESCs were grown on Matrigel in hESC culture media, as described in Example 1. PLGA microspheres, containing 0.5% FGF2, 3% $Mg(OH)_2$, 1:1 weight ratio of heparin to FGF2 and 1 mM EDTA ("FGF2 microspheres") were added to some cell culture wells to provide a sustained FGF2 level. 7 µl per 1 ml of culture media of FGF2-microsphere preparation (concentration 1000 microspheres per 1 µl of preparation) were used. In the control group (treated using the "standard method"), soluble human FGF2 was added every day at 10 ng/ml in fresh media at the time of media change. In other groups, FGF2-microspheres were added to the medium either once or twice a week.

Figure 6:
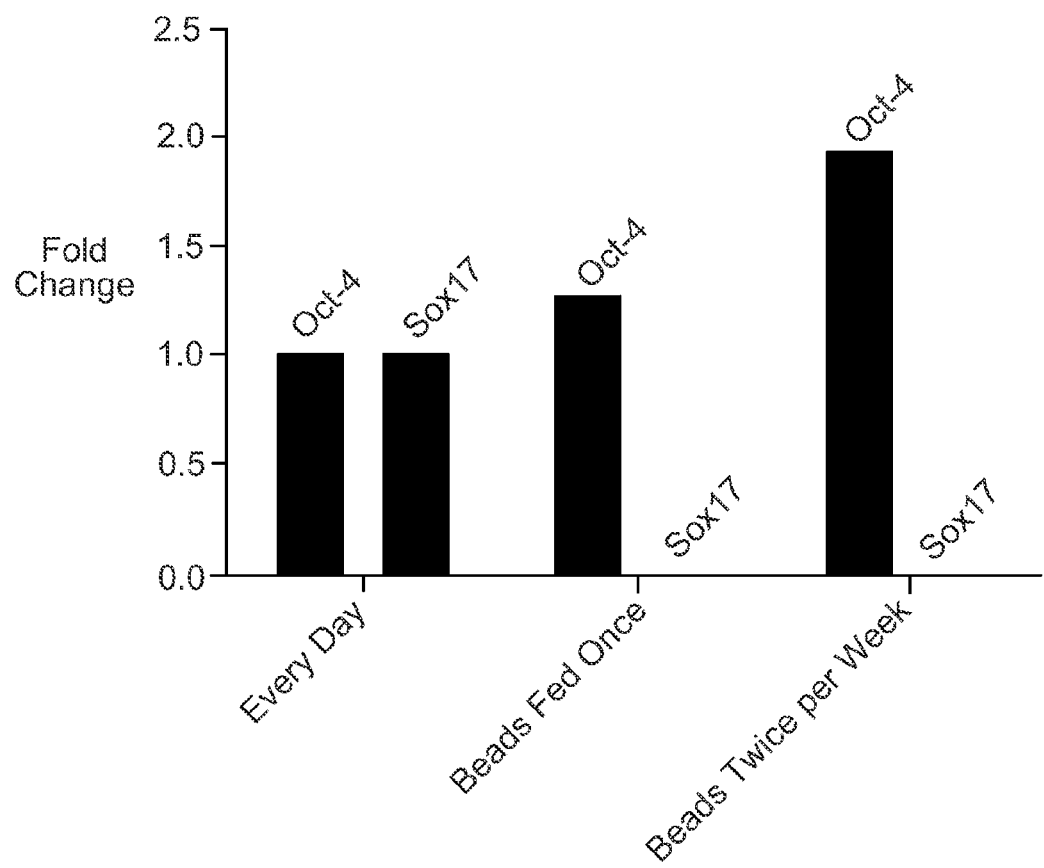
FIG. 6 is a graph showing the fold change in mRNA expression of Oct-4 and Sox17 in WA-09 hESCs cultured for 5 days on Matrigel in the presence of MEF-conditioned medium and either soluble FGF2 or FGF2-containing microspheres. In the control group, soluble FGF2 was added at a concentration of 10 ng/ml every day ("Every Day"). FGF2-containing PLGA microspheres were added to the cell culture once on Day 0 ("Beads Fed Once") or on Days 0 and 2 ("Beads Twice per Week").

The cells were grown for 5 days, and then mRNA expression levels of the pluripotency marker OCT-4 and the differentiation marker SOX17 were determined by quantitative RT-PCR. Cells cultured in the presence of FGF2 microspheres expressed higher OCT-4 levels than cells treated daily with soluble FGF2 (FIG. 6). Surprisingly, in all groups cultured in the presence of FGF2 microspheres, mRNA expression of the differentiation marker SOX17 was undetectable (FIG. 6). These data demonstrated that the stable, sustained FGF2 levels provided by a sustained release composition, such as FGF2 microspheres, can maintain hESCs in a more undifferentiated state without MEF feeder cells, MEF feeder conditioned medium, or specialized culture medium, as described above.

Example 6

Figure 7A:
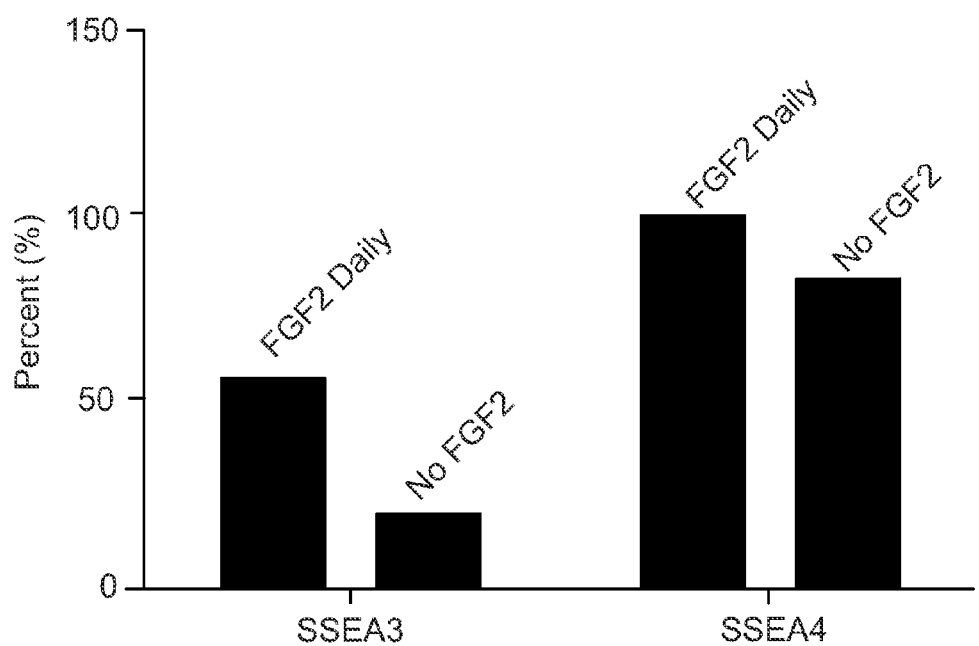
FIG. 7A is a graph showing the percent (%) of cells that stained positive for SSEA-3 or SSEA-4 protein on Day 7 in hESCs cultured with daily feeding of FGF2 ("FGF2 daily") or in hESCs plated in media containing 10 ng/ml FGF2 and then not fed again ("No FGF2").

Sustained FGF2 Levels Improved the Pluripotency of a Differentiated hESC Culture If cultured in media without FGF2, hESCs will slowly start to differentiate, gradually becoming less pluripotent. In this Example, it was tested whether sustained FGF2 levels could restore hESC pluripotency and make the culture more homogeneously pluripotent, in hESCs that had been allowed to differentiate.

hESCs were fed upon plating with complete culture medium, as described in Example 1, containing 10 ng/ml soluble FGF2 and then either fed soluble FGF2 every day ("FGF2 Daily") or not fed again ("No FGF2"), and left in culture for 7 days. On Day 7, cells were passaged according to standard procedures [see, Fasano et al., 2010, supra], and some cells were assessed for protein expression of the pluripotency markers SSEA-3 and SSEA-4. Expression of both SSEA-3 and SSEA-4, as determined by FACS analysis, was found to be decreased in the cells that did not receive daily FGF2 ("no FGF2" group) compared to expression of those markers in cells fed daily FGF2 ("FGF2 daily") (FIG. 7A).

Figure 7B:
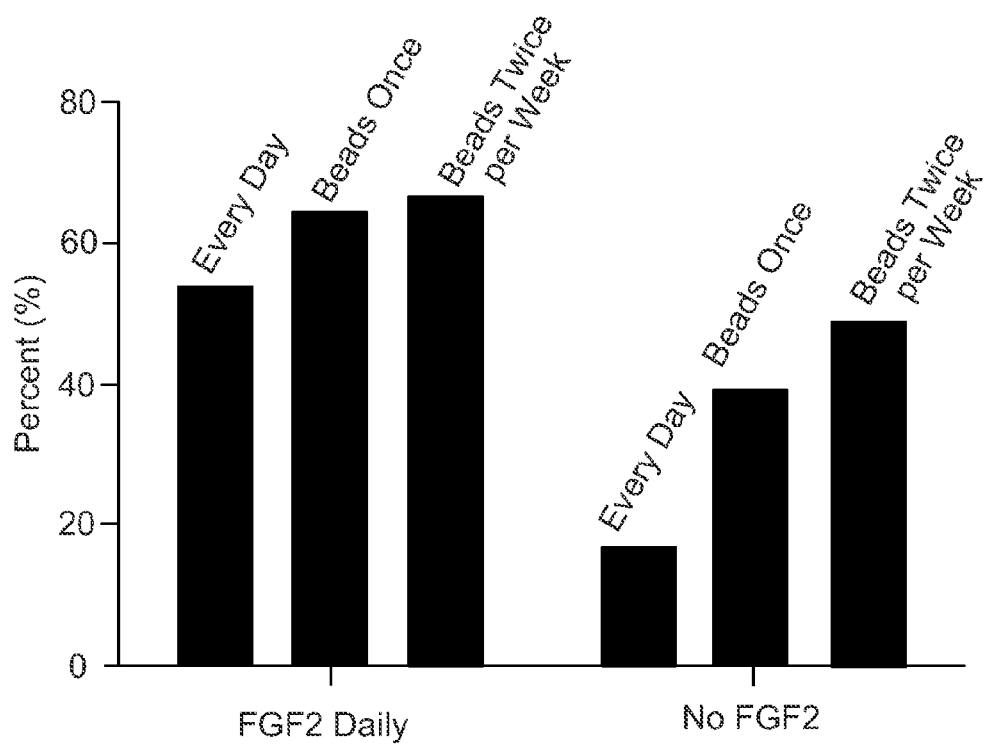
FIG. 7B is a graph showing the percent of cells in the "FGF2 daily" or "No FGF2" groups that stained positive for SSEA-3 protein following an additional 7 days of culture in the following conditions: cells were fed every day with 10 ng/ml FGF2 ("Every day"), or with FGF2 microspheres on Day 0 ("Once") or on Days 0 and 2 ("Beads Twice per Week").

At this point, the cells in both groups were re-plated, and regular FGF2-containing complete media or complete media containing FGF2-microspheres (containing 0.5% FGF2, 3% Mg(OH)$_2$, 1:1 weight ratio of heparin to FGF2 and 1 mM EDTA) were added to the cultures. 7 μl per 1 ml of culture media of FGF2-microsphere preparation (concentration 1000 microspheres per 1 μl of preparation) were used. Cells were fed every day with 10 ng/ml FGF2 ("Every Day" condition), or once (on Day 0) or twice (on Days 0 and 2) with FGF2-microspheres ("Beads Once" or "Beads Twice per Week" conditions, respectively). After 7 additional days of culture following re-plating, expression levels of SSEA3 were once again determined. SSEA-3 expression levels were higher in all groups cultured in the presence of FGF2-microspheres ("Beads Once" or "Beads Twice per Week" conditions), compared to cells fed daily with soluble FGF2 ("Every Day" condition). In the "no FGF2" group, every day feeding of soluble FGF2 following re-plating did not restore SSEA-3 back to control levels (i.e., the percentage of SSEA-3+ cells in the FGF2 Daily group fed every day with soluble FGF2 during the 7 additional days of culture), however, in the group of cells fed once with FGF2 microspheres, pluripotency (expression of SSEA-3) was partially rescued, and in the group fed FGF2-microspheres twice per week, pluripotency (expression of SSEA-3) of differentiated cells was nearly completely rescued, as compared to the control levels (FIG. 7B).

Example 7

Culture of NSCs with FGF2 PLGA Microspheres

Mouse NSCs were isolated from embryonic cortical brains and placed in culture and maintained as previously described [Qian et al, 1997, supra] or with modifications to that protocol, as described below. Briefly, in some wells, cells were plated in a basal medium supplemented with 10 ng/ml FGF2 and the media was changed every third day. This was the "standard condition." In other wells, NSCs were cultured in basic medium without soluble FGF2 in the presence of empty microspheres alone ("no FGF2", as in Example 3) to show that the microspheres alone are not mitogenic. In other wells, cells in basic medium without soluble FGF2 were cultured in the presence of PLGA microspheres containing 0.5% FGF2, 3% Mg(OH)$_2$, 1:1 weight ratio of heparin to FGF2 and 1 mM EDTA, and nothing more was added to these wells during culture (the culture media was not changed, and nothing was added to the culture after addition of the microspheres).

Figure 8:
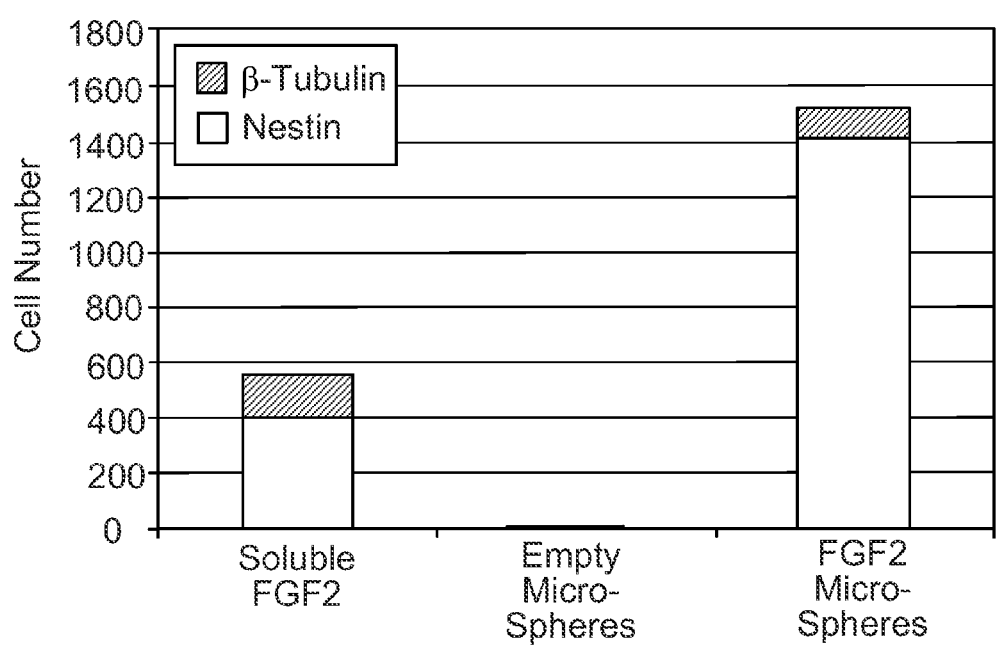
FIG. 8 is a graph showing the number of cells expressing β-tubulin or Nestin in the indicated treatment groups, 7 days after treatment of NSCs.

Following 7 days of treatment, cells were stained with Nestin- (DSHB) and β-tubulin- (Sigma-Aldrich) specific antibodies using standard staining techniques [see, Fasano et al., 2007, supra; and Fasano et al., 2009, Genes Dev. (2009) March 1; 23(5):561-74]. In the standard condition, cell clones generated as expected with a mix of NSCs and NPCs and neurons (differentiated cells) indicated by positive staining for Nestin (for NSCs and NPCs) or β-Tubulin (neurons (differentiated cells)). Specifically, cells fed with soluble FGF2 every third day gave rise to mixed clones with 380 NSCs and NPCs (Nestin+) and 170 neurons (β-tubulin+) (FIG. 8). Wells with the empty microspheres had less total cells, indicating poor survival with very little Nestin staining and loss of NSCs and NPCs (FIG. 8). In contrast, wells that had FGF2 containing microspheres ("FGF2 microspheres") added directly to them exhibited more clonal growth, with dramatically higher numbers of Nestin+ cells, indicating better NSC and NPCs growth. Specifically, one treatment with FGF2 containing microspheres increased cell number dramatically as well as the proportion of NSCs and NPCs: 1440 (Nestin+) to 120 neurons (β-tubulin) (FIG. 8).

Using standard (i.e., conventional) stem cell culture methods, the slow, steady differentiation of NSCs limits their usefulness. However, the novel methods discovered and described herein, in which a stable FGF2 concentration range was maintained over time in the stem cell culture using PLGA microspheres, resulted in the surprising decrease in spontaneous differentiation of cultured NSCs, thereby increasing the utility of these cells and significantly reducing the labor required to grow them. In one experiment, cells in additional wells were cultured in the standard condition and additionally with empty microspheres to determine whether the microspheres had any toxic effects on the cells. Addition of the empty microspheres to cells cultured under the standard condition did not affect the cells (i.e., was not toxic) compared to the standard condition. These data show that constant FGF2 exposure via steady delivery of FGF2 by the PLGA microspheres maintains NSCs and NPCs in the undifferentiated state surprisingly better than standard culture methods.

Example 8

Frequent Administration of FGF2 to NSCs

Figure 9:
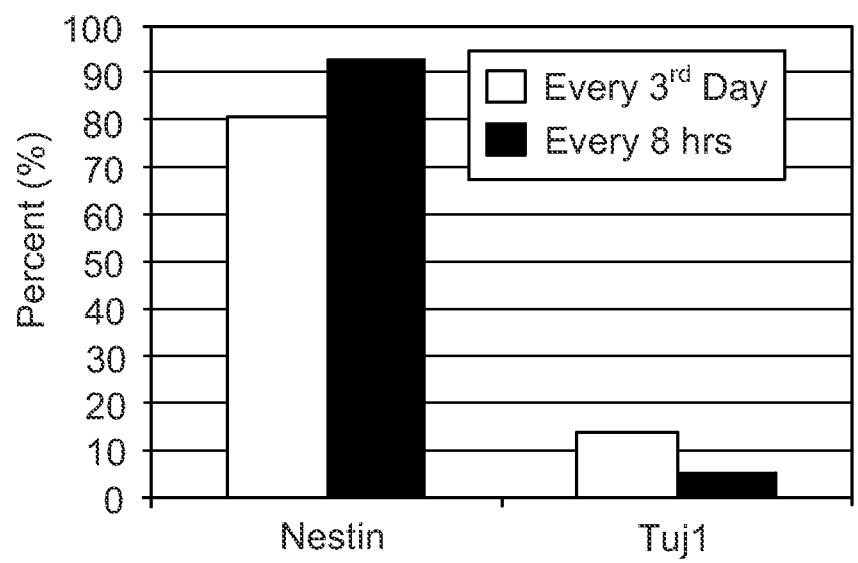
FIG. 9 is graph showing the number of cells expressing Nestin or β-tubulin in the indicated treatment groups, 6 days after treatment of NSCs with FGF2 according to the standard method (every 3rd day) or every 8 hours (hrs).

In this experiment, NSCs were fed every 8 hours with 10 ng/ml soluble human FGF2, to achieve a constant supply of FGF2, over 6 days. NSCs and NPCs maintain the stem or progenitor cell fate (i.e., remain in an undifferentiated state) by cell to cell interactions; loss of this contact initiates a differentiation response. Thus, tighter colonies are indicative of less differentiated NSCs and NPCs. Following frequent feeding (every 8 hours) of NSCs for 6 days, the NSC culture had tighter looking cells, indicative of undifferentiated cells. The NSC culture also had more Nestin staining, and less differentiation as measured by Tuj1 staining, compared to the standard method (feeding FGF2 every third day) (FIG. 9).

Example 9

Culture of Human RPESCs in Presence of Sustained Levels of FGF2

Figure 10:
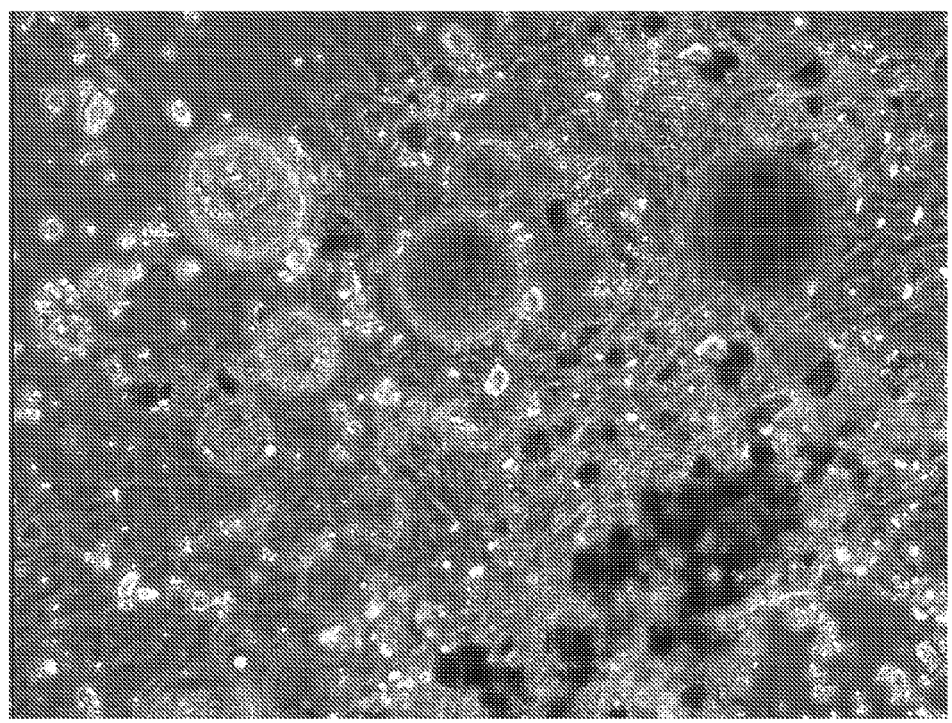
FIG. 10 is a photograph of RPESCs following 5 days of culture in the presence of FGF2-containing PLGA microspheres (32× magnification).

This example demonstrates the use of sustained FGF2 levels to propagate human retinal pigment epithelial stem cells (RPESCs) in culture. RPESCs were isolated as follows:
Dissection Human eyes from 22-99 year old donors were obtained from The Eye-Bank for Sight Restoration, Inc. (New York, N.Y.), and the National Disease Research Interchange (NDRI) (Philadelphia, Pa.). The eyes were cut at the ora serrata and the anterior segment discarded. The vitreous and retina were removed leaving the RPE layer exposed. RPE dissection and single cell dissociation was performed as previously described [see, U.S. Patent Application Publication No. 2009/0274667 by Temple; Burke, C. M. et al., Exp Eye Res 62, 63 (1996); and Maminishkis, A. et al., Invest Ophthalmol V is Sci 47, 3612 (2006)]. Gentle trituration within the eyecup using care to maintain Bruch's membrane yielded a suspension of RPE cells with minimal contamination by rod outer segments, blood or other cell types.
RPE Sheet Dissection and Cobblestone Culture After the vitreous and retina were separated as described above, the eyecup was rinsed with sterile PBS and then incubated with cell dissociation buffer enzyme-free Hanks'-based (Gibco-Invitrogen, Carlsbad, Calif.) for 10 minutes at 37° C. Gently the dissociation buffer was removed and the eyecup filled with DMEM/F12 media supplemented with 20% FBS (Gibco-Invitrogen). Using a dulled, angled, double bevel spoon blade (3.0 mm), small sheets (1 mm$^2$) of RPE were removed from the Bruch's membrane by gentle scraping. RPE sheets were plated into Matrigel (BD Biosciences) pretreated tissue culture plates and cultured in RPE medium: MEM-α modified medium (Sigma-Aldrich), 2 mM L-glutamine, penicillin/streptomycin (1:100), 1% Na-Pyruvate, 10% FBS (fetal bovine serum), supplemented with THT (Taurine Hydrocortisone, Triiodo-thyronin) and N1 (Sigma-Aldrich) as described [De, S. et al. Arch Ophthalmol. 2007; May; 125(5):641-5; Burke et al., 1996, supra; and Maminishkis, A. et al., 2006, supra] with 10 ng/ml FGF2 and 1 ng/ml EGF (Gibco-Invitrogen).
Culture Using a defined medium growth medium containing MEM-α modified medium (Sigma-Aldrich), 2 mM L-glutamine, penicillin/streptomycin (1:100), 1% Na-Pyruvate, 10% FBS (fetal bovine serum), supplemented with THT (Taurine Hydrocortisone, Triiodo-thyronin) and N1 (Sigma-Aldrich) and supplemented with 7 μl per 1 ml of culture media of FGF2-containing PLGA microspheres (containing 0.5% FGF2, 3% Mg(OH)$_2$, 1:1 weight ratio of heparin to FGF2 and 1 mM EDTA), the RPESCs were grown for 5 days. Cells were grown according to the methods described in detail in U.S. Patent Application Publication No. 2009/0274667 by Temple et al. After 5 days, the cells were photographed and displayed normal morphology and growth patterns compared to medium with soluble FGF2 (FIG. 10).

Example 10

Generation of iPSCs in the Presence of FGF2

Figure 11:
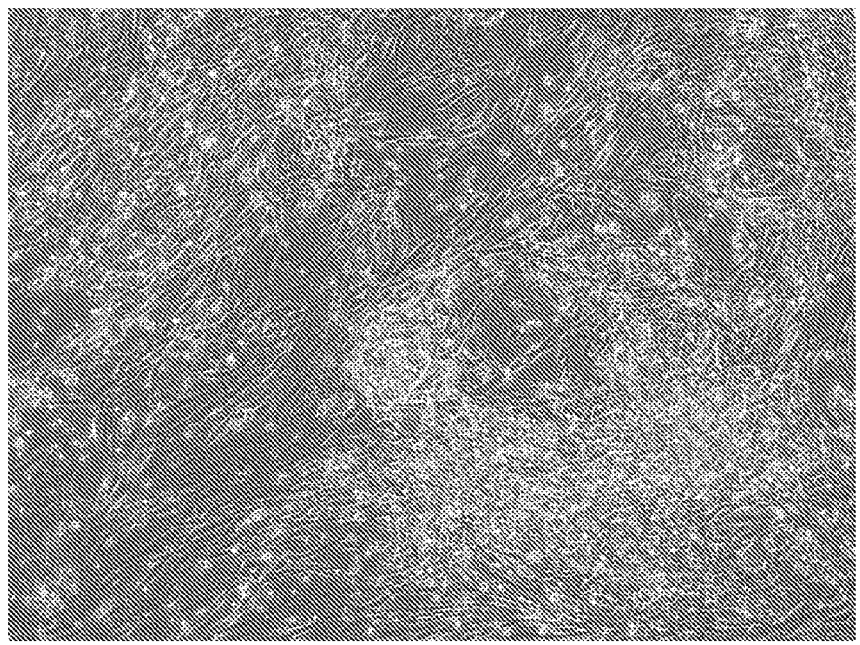
FIG. 11 contains photographs of iPSCs taken 9 days after the cells were plated and cultured with daily addition of soluble FGF2 (upper panel) or with the addition of FGF2-containing PLGA microspheres on Days 0 and 3 (lower panel) (20× magnification).
Figure 11:
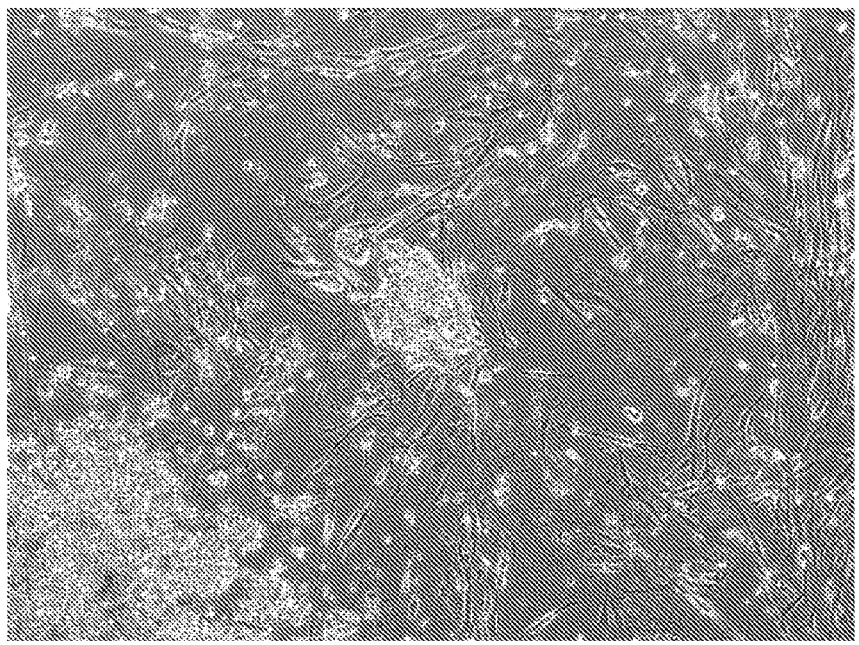

This example demonstrates the use of sustained FGF2 levels for the generation of induced pluripotent stem cells (iPSCs). Adult fibroblasts were infected with retroviral supernatant containing OCT4, KLF4, c-MYC and SOX2, according to the methods described in Takahashi, K. et al. (2007); Cell 131, 861-872. 10 days after infection, cells were trypsinized and counted and 10$^5$ cells were plated onto MEFs in DMEM+10% FBS. The day after, media was replaced with standard hESC media (DMEM/F12 (Invitrogen, Carlsbad, Calif.)), containing L-Glutamine (Invitrogen), Minimal Essential Amino Acids (Invitrogen), 20% Knockout Serum Replacement (Invitrogen), and 2-Mercaptoethanol (Invitrogen))+4 ng/ml FGF2 ("soluble FGF2" group) or with hESC media containing FGF2-containing PLGA microspheres (containing 0.5% FGF2, 3% Mg(OH)$_2$, 1:1 weight ratio of heparin to FGF2 and 1 mM EDTA) ("FGF2-microspheres" group). In the soluble FGF2 group, the media was replaced daily, while media containing FGF2-containing PLGA microspheres was changed twice per week (the fresh media added to the cultures at the time of media change contained FGF2-microspheres). Pictures were taken 9 days after cells were plated. In the condition with daily feeds and soluble FGF2, cells were observed to have no distinct colony size or formation (FIG. 11, left panel). In contrast, cells cultured in the presence of FGF2-microspheres had colonies that exhibited characteristics of human embryonic stem cell colonies (FIG. 11, right panel), demonstrating that culture of iPSCs in the presence of sustained levels of FGF2 increased the efficiency of iPSC generation.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are incorporated by reference in their entirety as if physically present in this specification and to the same extent as if each item had been incorporated by reference individually. However, the citation of any such material, even in discussing the Background of this invention, is not to be construed as an admission that the material was or is available as prior art to the present invention.

What is claimed is:

1. A method for culturing a stem or progenitor cell, which method comprises:
   (a) adding, to a culture of stem or progenitor cells, a sustained release composition comprising at least one growth factor that maintains the cells in an undifferentiated state; and
   (b) repeating the step of adding the sustained release composition such that the cells are maintained in an undifferentiated state.

2. The method of claim 1, wherein the sustained release composition is added to the culture at least once a week.

3. The method of claim 1, wherein the sustained released composition is added to the culture not more often than every other day.

4. The method of claim 1, wherein the sustained release composition is added to the culture not more often than every three days.

5. The method of claim 1, wherein the sustained release composition comprises at least one growth factor selected from the group consisting of: epidermal growth factor (EGF), platelet-derived growth factor (PDGF), sonic hedgehog (Shh), leukemia inhibitor factor (LIF), Wnt protein, and fibroblast growth factor 2 (FGF2).

6. The method of claim 1, wherein the sustained release compositions comprises at least fibroblast growth factor 2 (FGF2).

7. The method of claim 6, wherein the sustained release composition further comprises one or more additional growth factors.

8. The method of claim 7, wherein the one or more additional growth factors include one or more growth factors selected from the group consisting of: epidermal growth factor (EGF), platelet-derived growth factor (PDGF), sonic hedgehog (Shh), leukemia inhibitor factor (LIF) and Wnt protein.

9. The method of claim 1, wherein the sustained release composition comprises poly(D-lactide-co-glycolide) (PLGA) microspheres.

10. The method of claim 1, wherein the cells are maintained in an undifferentiated state for at least about two weeks.

11. The method of claim 1, wherein the cells comprise one or more cells selected from the group consisting of: embryonic stem cells, induced pluripotent stem cells, neural stem cells, retinal pigment epithelial stem cells, hematopoietic stem cells, mesenchymal stem cells, cancer stem cells and epiblast stem cells.

12. The method of claim 1, wherein the cells comprise human embryonic stem cells.

13. The method of claim 1, wherein the cells comprise neural progenitor cells.

14. The method of claim 1, wherein the sustained release composition releases the growth factor into the cell culture such that a concentration of the growth factor is maintained, the concentration being about 80-100% of a starting concentration.

15. The method of claim 1, wherein cells maintain a higher expression level of OCT4, Nanog or Nestin compared to when the sustained release composition is not added.

16. The method of claim 15, wherein the higher expression level of OCT4, Nanog or Nestin is maintained for two or more weeks.

17. The method of claim 1, wherein the cells maintain a lower expression level of SOX17, Brachyury or SSEA-1 compared to when the sustained release composition is not added.

18. The method of claim 17, wherein the lower expression level of SOX17, Brachyury or SSEA-1 is maintained for two or more weeks.

* * * * *